(12) United States Patent
Hu et al.

(10) Patent No.: US 12,630,525 B2
(45) Date of Patent: May 19, 2026

(54) TRIAZINYLMETHYLCYCLOALKYL-CARBOXYLIC ACID DERIVATIVE, AND PHARMACEUTICAL COMPOSITION AND USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Bin Hu, Shanghai (CN); Jingfeng Zhu, Shanghai (CN); Wen Yang, Shanghai (CN); Jing Xie, Shanghai (CN); Xiaoyong Shi, Shanghai (CN); Kai Zhang, Shanghai (CN); Zhiming Zhao, Shanghai (CN); Chao Kan, Shanghai (CN)

(73) Assignees: Shanghai Haiyan Pharmaceutical Technology Co., Ltd., Shanghai (CN); Yangtze River Pharmaceutical Group Co., Ltd., Jiangsu (CN)

( * ) Notice: Subject to any disclaimer, the term of this patent is extended or adjusted under 35 U.S.C. 154(b) by 378 days.

(21) Appl. No.: 18/565,245

(22) PCT Filed: Jun. 1, 2022

(86) PCT No.: PCT/CN2022/096597

§ 371 (c)(1),
(2) Date: Nov. 29, 2023

(87) PCT Pub. No.: WO2022/253270

PCT Pub. Date: Dec. 8, 2022

(65) Prior Publication Data

US 2024/0287026 A1 Aug. 29, 2024

(30) Foreign Application Priority Data

Jun. 4, 2021 (CN) ......................... 202110625932.5
Jan. 27, 2022 (CN) ......................... 202210103237.7

(51) Int. Cl.

| | |
|---|---|
| ***C07D 401/12*** | (2006.01) |
| ***A61K 31/53*** | (2006.01) |
| ***A61P 29/00*** | (2006.01) |

(52) U.S. Cl.
CPC ............ *C07D 401/12* (2013.01); *A61K 31/53* (2013.01); *A61P 29/00* (2018.01)

(58) Field of Classification Search
CPC ........ C07D 401/12; A61P 29/00; A61K 31/53
See application file for complete search history.

(56) References Cited

FOREIGN PATENT DOCUMENTS

| | | | |
|---|---|---|---|
| CN | 102395571 | A | 3/2012 |
| CN | 103153968 | A | 6/2013 |
| EP | 3009432 | A1 | 4/2016 |
| WO | 2013089212 | A1 | 6/2013 |
| WO | 2017204316 | A1 | 11/2017 |

OTHER PUBLICATIONS

Extended European Search Report mailed on Apr. 24, 2025, in European Application No. 22815312.8.

*Primary Examiner* — Kamal A Saeed
*Assistant Examiner* — Quincy Mckoy
(74) *Attorney, Agent, or Firm* — Meunier Carlin & Curfman LLC

(57) ABSTRACT

A substituted triazinylmethylcycloalkylcarboxylic acid derivative having a structure as shown in formula (I). In addition, further disclosed are a pharmaceutically acceptable salt, a stereoisomer, a pharmaceutical composition and the use of the derivative. The compound has significant P2X3 inhibitory activity and selectivity, and is high in application value.

(I)

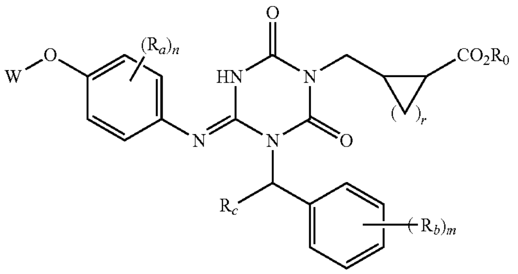

19 Claims, 1 Drawing Sheet

TRIAZINYLMETHYLCYCLOALKYL-CARBOXYLIC ACID DERIVATIVE, AND PHARMACEUTICAL COMPOSITION AND USE THEREOF

CROSS REFERENCE TO RELATED APPLICATIONS

This application is a U.S. National Stage application filed under 35 U.S.C. 371 of PCT/CN2022/096597, filed on Jun. 1, 2022, which claims the benefit of Chinese Patent Application No. 202110625932.5, filed on Jun. 4, 2021, and Chinese Patent Application No. 202210103237.7, filed on Jan. 27, 2022.

TECHNICAL FIELD

The present application relates to the technical field of medicine, in particular to a triazinylmethylcycloalkylcarboxylic acid derivative, and a pharmaceutically acceptable salt, a stereoisomer, a pharmaceutical composition and medical use thereof.

BACKGROUND

P2X purine receptors are a family of ion channels activated by extracellular adenosine triphosphate (ATP). Purine receptors are involved in a variety of biological functions, especially those related to pain sensitivity. The P2X3 receptor is a member of this family and was originally cloned from the rat dorsal root ganglion (Chen et al., Nature, vol. 377, pp. 428-431 (1995)). The nucleotide and amino acid sequences of both rat P2X3 and human P2X3 are now known (Lewis et al., Nature, vol. 377, pp. 432-435 (1995); and Garcia-Guzman et al., Brainres. mol. BrainRes., vol. 47, pp. 59-66 (1997)).

P2X3 is reported to be involved in afferent pathways that control bladder volume reflexes. Therefore, inhibiting P2X3 could treat conditions related to urine storage and urination, such as overactive bladder (Cockayne et al., Nature, vol. 407, pp. 1011-1015 (2000)).

P2X3 is also selectively expressed on nociceptive neurons and small diameter sensory neurons (i.e. neurons stimulated by pain or injury), which is consistent with its role in pain sensitivity. In addition, blocking P2X3 receptors has been reported to have an analgesic effect in animal models of chronic inflammatory and neuropathologic pain (Jarvis et al., PNAS, 99, 17179-17184 (2002)). Therefore, methods to reduce the level or activity of P2X3 can be used to modulate pain perception of subjects in pain.

P2X3 is also capable of forming a P2X2/3 heterodimer with P2X2, another member of the P2X purinergic ligand-gated ion channel family. P2X2/3 is highly expressed on sensory neurons endings (central and peripheral) (Chen et al., Nature, vol. 377, pp. 428-431 (1995)). Recent findings also suggest that P2X2/3 is expressed primarily in bladder sensory neurons (exceeding P2X3) and may play a role in the perception of bladder fullness and nociceptive sensations (Zhong et al., Neuroscience, vol. 120, pp. 667-675 (2003)).

Therefore, there is a need to provide a potentially useful new ligand of P2X3 and/or P2X2/3 receptor, especially an antagonist, for the treatment of various conditions associated with P2X3 and/or P2X2/3.

SUMMARY

The application aims to provide a structurally novel triazinylmethylcycloalkylcarboxylic acid derivative, or a pharmaceutically acceptable salt thereof, or a stereoisomer thereof, a pharmaceutical composition thereof, and use thereof as a P2X3 antagonist. These compounds have high inhibitory activity against P2X3 and low inhibitory activity against P2X2/3, and have significant inhibitory selectivity.

A first aspect of the application provides a compound represented by formula (I), or a pharmaceutically acceptable salt thereof, or a stereoisomer thereof:

(I)

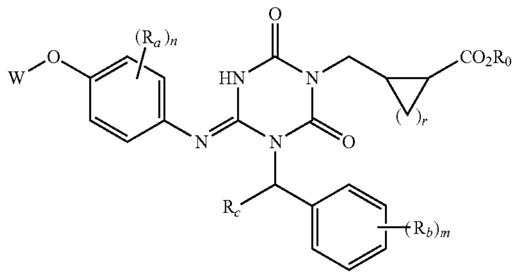

wherein, r is 1, 2, or 3;

W is a benzene ring or a 5- to 6-membered heteroaryl ring (preferably pyridine ring); the benzene ring and the 5- to 6-membered heteroaryl ring (preferably pyridine ring) are unsubstituted or substituted by 1, 2, 3, or 4 substituents each independently selected from the following group consisting of: deuterium, halogen (preferably fluorine, chlorine), cyano, hydroxyl, carboxyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), $C_{2-4}$ alkenyl, $C_{2-4}$ alkynyl, halo-$C_{1-8}$ alkyl (preferably halo-$C_{1-6}$ alkyl, more preferably halo-$C_{1-3}$ alkyl), cyano-substituted $C_{1-8}$ alkyl (preferably cyano-substituted $C_{1-6}$ alkyl, more preferably cyano-substituted $C_{1-3}$ alkyl), halo-$C_{1-8}$ alkoxy (preferably halo-$C_{1-6}$ alkoxy, more preferably halo-$C_{1-3}$ alkoxy), $NR_{a0}R_{b0}$, —$SO_2C_{1-3}$ alkyl, —$S(O)C_{1-3}$ alkyl, —$C(O)NR_{a1}R_{b1}$, —$C(O)C_{1-8}$ alkyl (preferably —$C(O)C_{1-6}$ alkyl, more preferably —$C(O)C_{1-3}$ alkyl), —$C(O)OC_{1-8}$ alkyl (preferably —$C(O)OC_{1-6}$ alkyl, more preferably —$C(O)OC_{1-3}$ alkyl), —$OC(O)C_{1-8}$ alkyl (preferably —$OC(O)C_{1-6}$ alkyl, more preferably —$OC(O)C_{1-3}$ alkyl), $C_{3-6}$ cycloalkyl, $C_{3-6}$ cycloalkyloxy, 3- to 6-membered heterocycloalkyl, phenyl, and 5- to 6-membered heteroaryl; wherein, among the substituents, the 3- to 6-membered heterocycloalkyl, phenyl, and 5- to 6-membered heteroaryl are unsubstituted or substituted by 1, 2, or 3 substituents each independently selected from the following group consisting of: halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkyloxy, 3- to 6-membered heterocycloalkyl, phenyl, and 5- to 6-membered heteroaryl;

$(R_a)_n$ represents that hydrogen(s) on benzene ring is/are substituted with n $R_a$, and n is 0, 1, or 2; each $R_a$ is identical or different, and each $R_a$ is independently cyano, hydroxyl, carboxyl, halogen (preferably fluorine or chlorine), $C_{1-8}$ alkyl (preferably $C_{1-6}$ alkyl, more preferably $C_{1-3}$ alkyl), halo-$C_{1-8}$ alkyl (preferably halo- $C_{1-6}$ alkyl, more preferably halo-$C_{1-3}$ alkyl), cyano-substituted $C_{1-8}$ alkyl (preferably cyano-substituted $C_{1-6}$ alkyl, more preferably cyano-substituted $C_{1-3}$ alkyl), $C_{1-8}$ alkoxy (preferably $C_{1-6}$ alkoxy, more preferably $C_{1-3}$ alkoxy), —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —OC(O)$C_{1-8}$ alkyl (preferably —OC(O)$C_{1-6}$ alkyl, more preferably —OC(O)$C_{1-3}$ alkyl), or —C(O)$NR_{a1}R_{b1}$;

$R_c$ is hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), $C_{1-8}$ alkoxy (preferably $C_{1-6}$ alkoxy, more preferably $C_{1-3}$ alkoxy), cyano, hydroxyl, carboxyl, or halogen (preferably fluorine or chlorine);

$(R_b)_m$ represents that hydrogen(s) on benzene ring is/are substituted with m $R_b$, and m is 0, 1, or 2; each $R_b$ is identical or different, and each $R_b$ is independently cyano, hydroxyl, carboxyl, halogen (preferably fluorine or chlorine), $C_{1-8}$ alkyl (preferably $C_{1-6}$ alkyl, more preferably $C_{1-3}$ alkyl), halo-$C_{1-8}$ alkyl (preferably halo-$C_{1-6}$ alkyl, more preferably halo-$C_{1-3}$ alkyl), cyano-substituted $C_{1-8}$ alkyl (preferably cyano-substituted $C_{1-6}$ alkyl, more preferably cyano-substituted $C_{1-3}$ alkyl), $C_{1-8}$ alkoxy (preferably $C_{1-6}$ alkoxy, more preferably $C_{1-3}$ alkoxy), —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —OC(O)$C_{1-8}$ alkyl (preferably —OC(O)$C_{1-6}$ alkyl, more preferably —OC(O)$C_{1-3}$ alkyl), or —C(O)$NR_{a1}R_{b1}$;

$R_0$ is hydrogen or $C_{1-6}$ alkyl;

$R_{a1}$ and $R_{b1}$ are each independently hydrogen or $C_{1-3}$ alkyl; or $R_{a1}$, $R_{b1}$ and nitrogen atom linked to $R_{a1}$ and $R_{b1}$ together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —S(O)$C_{1-3}$ alkyl, —C(O)$NH_2$, —C(O)NH($C_{1-3}$ alkyl), —C(O)N($C_{1-3}$ alkyl)$_2$, —C(O)O$C_{1-3}$ alkyl, —OC(O)$C_{1-3}$ alkyl, $C_{3-6}$ cycloalkyl, $C_{3-6}$ cycloalkyloxy, and 3- to -6-membered heterocycloalkyl; and $R_{a0}$ and $R_{b0}$ are each independently hydrogen, $C_{1-3}$ alkyl, or acetyl; or $R_{a0}$, $R_{b0}$ and nitrogen atom linked to $R_{a0}$ and $R_{b0}$ together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —S(O)$C_{1-3}$ alkyl, —C(O)$NH_2$, —C(O)NH($C_{1-3}$ alkyl), —C(O)N($C_{1-3}$ alkyl)$_2$, —C(O)O$C_{1-3}$ alkyl, —OC(O)$C_{1-3}$ alkyl, $C_{3-6}$ cycloalkyl, $C_{3-6}$ cycloalkyloxy, and 3- to -6-membered heterocycloalkyl.

In some embodiments, r is 1.

In some embodiments, W is

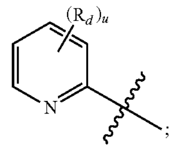

$(R_d)_u$ represents that hydrogen(s) on pyridine ring is/are substituted with u $R_d$, and u is 0, 1, or 2; each $R_d$ is identical or different, and each $R_d$ is independently deuterium, halogen (preferably fluorine, chlorine), cyano, hydroxyl, carboxyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), $C_{2-4}$ alkenyl, $C_{2-4}$ alkynyl, halo-$C_{1-8}$ alkyl (preferably halo-$C_{1-6}$ alkyl, more preferably halo-$C_{1-3}$ alkyl), halo-$C_{1-8}$ alkoxy (preferably halo-$C_{1-6}$ alkoxy, more preferably halo-$C_{1-3}$ alkoxy), $NR_{a0}R_{b0}$, —$SO_2C_{1-3}$ alkyl, —S(O)$C_{1-3}$ alkyl, —C(O)$NR_{a1}R_{b1}$, —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —OC(O)$C_{1-8}$ alkyl (preferably —OC(O)$C_{1-6}$ alkyl, more preferably —OC(O)$C_{1-3}$ alkyl), $C_{3-6}$ cycloalkyl, $C_{3-6}$ cycloalkyloxy, 3- to 6-membered heterocycloalkyl, phenyl, or 5- to 6-membered heteroaryl; wherein, among the substituents, the 3- to 6-membered heterocycloalkyl, phenyl, and 5- to 6-membered heteroaryl are unsubstituted or substituted by 1, 2, or 3 substituents each independently selected from the following group consisting of: halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, $NR_{a0}R_{b0}$, —$SO_2C_{1-3}$ alkyl, —S(O)$C_{1-3}$ alkyl, —C(O)$NR_{a1}R_{b1}$, —C(O)O$C_{1-3}$ alkyl, —OC(O)$C_{1-3}$ alkyl, $C_{3-6}$ cycloalkyl, $C_{3-6}$ cycloalkyloxy, 3- to 6-membered heterocycloalkyl, phenyl, and 5- to 6-membered heteroaryl.

In some embodiments, u is 0 or 1; and $R_d$ is fluorine, chlorine, cyano, hydroxyl, carboxyl, $C_{1-3}$ alkyl (preferably methyl, ethyl, n-propyl, or isopropyl), $C_{1-3}$ alkoxy (preferably methoxy), halo-$C_{1-3}$ alkyl (preferably monofluoromethyl, difluoromethyl, or trifluoromethyl), halo-$C_{1-3}$ alkoxy (preferably monofluoromethoxy, difluoromethoxy, or trifluoromethoxy), $NR_{a0}R_{b0}$, —$SO_2C_{1-3}$ alkyl, —S(O)$C_{1-3}$ alkyl, —C(O)$NR_{a1}R_{b1}$, —C(O)$C_{1-3}$ alkyl, —C(O)O$C_{1-3}$ alkyl, or —OC(O)$C_{1-3}$ alkyl.

In some embodiments, $R_d$ contains an electron withdrawing group.

In some embodiments, $R_d$ is an electron withdrawing group.

In some embodiments, $R_d$ is electron withdrawing group substituted $C_{1-8}$ alkyl; further, $R_d$ is halo-$C_{1-8}$ alkyl.

In some embodiments, u is 0 or 1, and $R_d$ is halogen (preferably fluorine) or halo-$C_{1-3}$ alkyl (preferably monofluoromethyl, difluoromethyl, or trifluoromethyl); further, $R_d$ is fluorine.

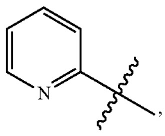,

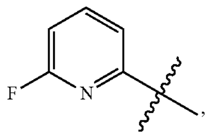,

-continued

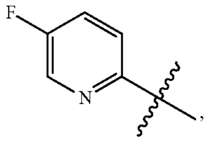,
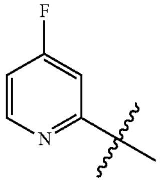,
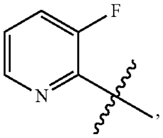,
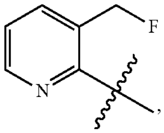,
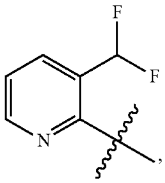,
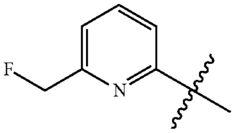 or
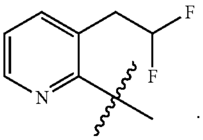.

In some embodiments, W is

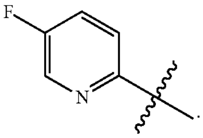.

In some embodiments, m is 0 or 1; and $R_b$ is cyano, hydroxyl, carboxyl, fluorine, chlorine, $C_{1-3}$ alkyl, $C_{1-3}$ alkoxy, —C(O)$C_{1-3}$ alkyl, —C(O)O$C_{1-3}$ alkyl, —OC(O) $C_{1-3}$ alkyl, or —C(O)N$R_{a1}R_{b1}$.

In some embodiments, $R_b$ is an electron withdrawing group.

In some embodiments, m is 1 and $R_b$ is halogen or cyano; further, $R_b$ is chlorine.

In some embodiments, m is 1 and $R_b$ is para-substitution.

In some embodiments,

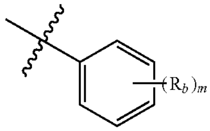

is

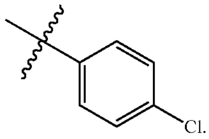 [SMILES: *c1ccc(Cl)cc1]

In some embodiments, n is 0 or 1; and $R_a$ is cyano, hydroxyl, carboxyl, fluorine, chlorine, $C_{1-3}$ alkyl, $C_{1-3}$ alkoxy, —C(O)$C_{1-3}$ alkyl, —C(O)O$C_{1-3}$ alkyl, —OC(O) $C_{1-3}$ alkyl, or —C(O)N$R_{a1}R_{b1}$.

In some embodiments,

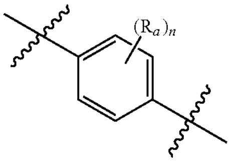

is

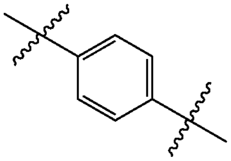

or

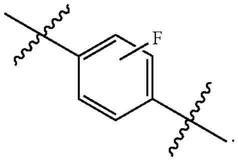.

In some embodiments, n is 0.

In some embodiments, $R_c$ is hydrogen, $C_{1-3}$ alkyl, $C_{3-6}$ cycloalkyl, $C_{1-3}$ alkoxy, cyano, hydroxyl, carboxyl, fluorine, chlorine, —C(O)N$R_{a1}R_{b1}$, —C(O)$C_{1-3}$ alkyl, or —C(O) O$C_{1-3}$ alkyl.

In some embodiments, $R_c$ is hydrogen.

In some embodiments, $R_0$ is hydrogen.

In some embodiments, $R_0$ is $C_{1-6}$ alkyl; further, $R_0$ is $C_{1-4}$ alkyl.

In some embodiments,

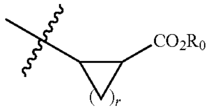

in the structure of formula (I) is in a form of a cis-structure.

In some embodiments,

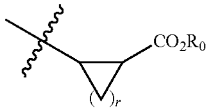

in the structure of formula (I) is in a form of a trans-structure.

In some embodiments, the compound of formula (I) is of the structure shown in formula (II):

(II)

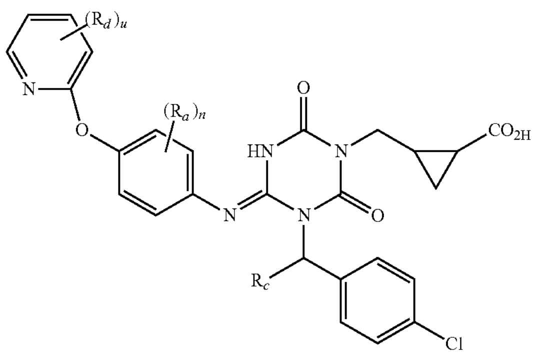

wherein, $R_a$, $R_c$, $R_d$, n, and u are as defined above.

In some embodiments,

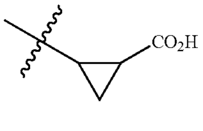 [SMILES: *C1CC1C(=O)O]

in the structure of formula (II) is in a form of a cis-structure.

In some embodiments,

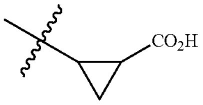 [SMILES: *C1CC1C(=O)O]

in the structure of formula (II) is in a form of a trans-structure.

In some embodiments, the compound of formula (I) is of the structure shown in formula (II-1):

(II-1)

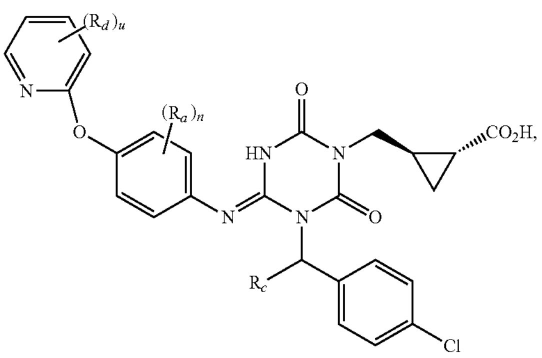

wherein, $R_a$, $R_c$, $R_d$, n, and u are as defined above.

In some embodiments, the compound of formula (I) is of the structure shown in formula (II-2):

(II-2)

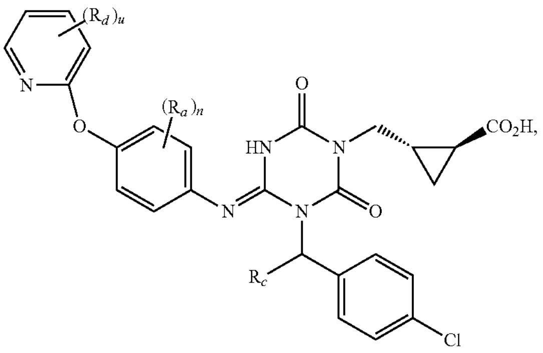

wherein, $R_a$, $R_c$, $R_d$, n, and u are as defined above.

In some embodiments, the compound of formula (I) is of the structure shown in formula (II-3):

(II-3)

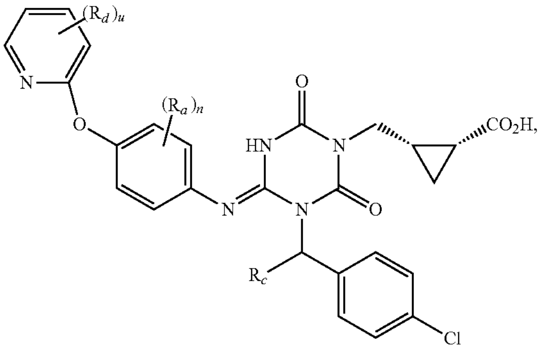

wherein, $R_a$, $R_b$, $R_d$, n, and u are as defined above.

In some embodiments, the compound of formula (I) is of the structure shown in formula (II-4):

(II-4)

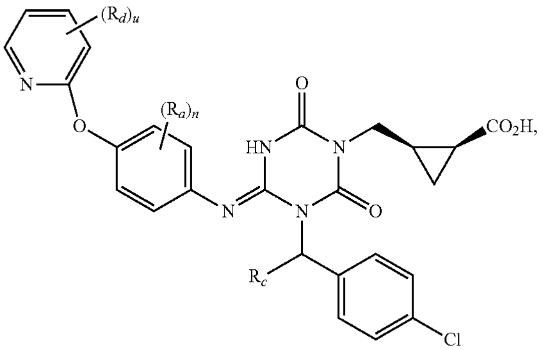

wherein, $R_a$, $R_c$, $R_d$, n, and u are as defined above.

In some embodiments, the compound of formula (I) is a specific compound listed in examples.

In some embodiments, the compound of formula (I) is a compound selected from those in Table 1 or a stereoisomer thereof:

TABLE 1
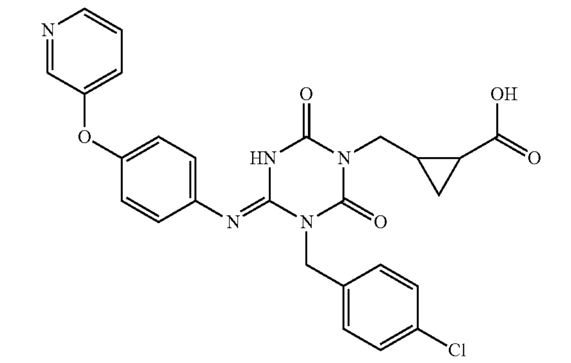 [SMILES: O=C(O)C1CC1Cn1c(=O)[nH]/c(=N\c2ccc(Oc3cccnc3)cc2)n(Cc2ccc(Cl)cc2)c1=O]
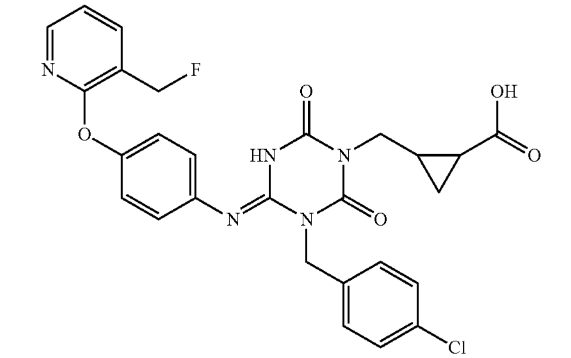 [SMILES: O=C(O)C1CC1Cn1c(=O)[nH]/c(=N\c2ccc(Oc3ncccc3CF)cc2)n(Cc2ccc(Cl)cc2)c1=O]
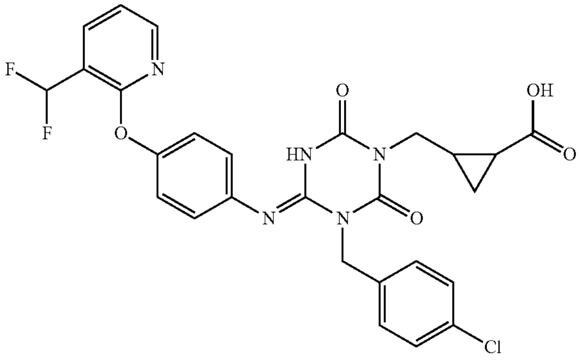 [SMILES: O=C(O)C1CC1Cn1c(=O)[nH]/c(=N\c2ccc(Oc3ncccc3C(F)F)cc2)n(Cc2ccc(Cl)cc2)c1=O]
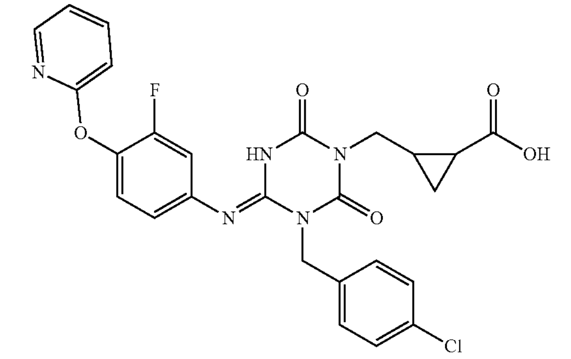 [SMILES: O=C(O)C1CC1Cn1c(=O)[nH]/c(=N\c2ccc(Oc3ccccn3)c(F)c2)n(Cc2ccc(Cl)cc2)c1=O]
TABLE 1-continued
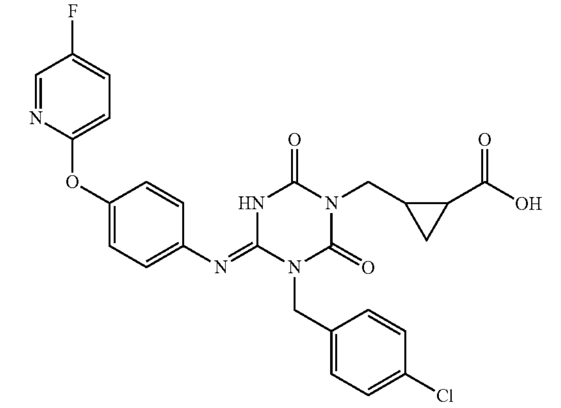 [SMILES: O=C(O)C1CC1Cn1c(=O)[nH]/c(=N\c2ccc(Oc3ccc(F)cn3)cc2)n(Cc2ccc(Cl)cc2)c1=O]
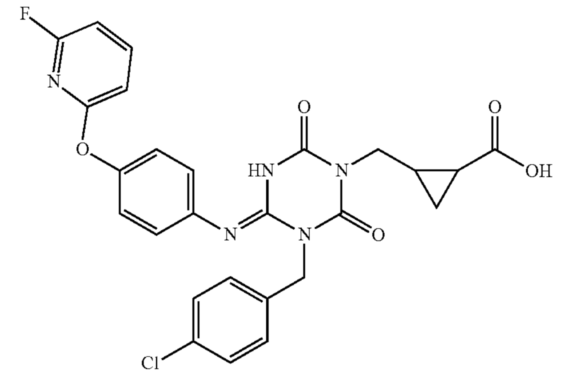 [SMILES: O=C(O)C1CC1Cn1c(=O)[nH]/c(=N\c2ccc(Oc3cccc(F)n3)cc2)n(Cc2ccc(Cl)cc2)c1=O]
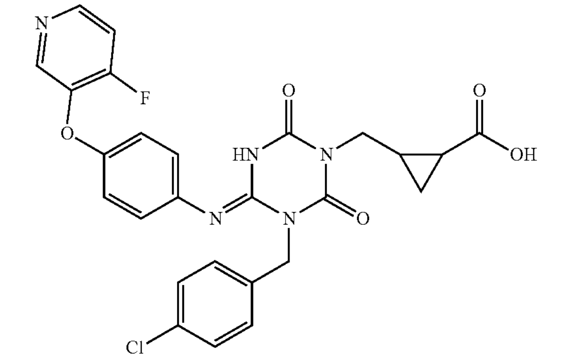 [SMILES: O=C(O)C1CC1Cn1c(=O)[nH]/c(=N\c2ccc(Oc3cnccc3F)cc2)n(Cc2ccc(Cl)cc2)c1=O]
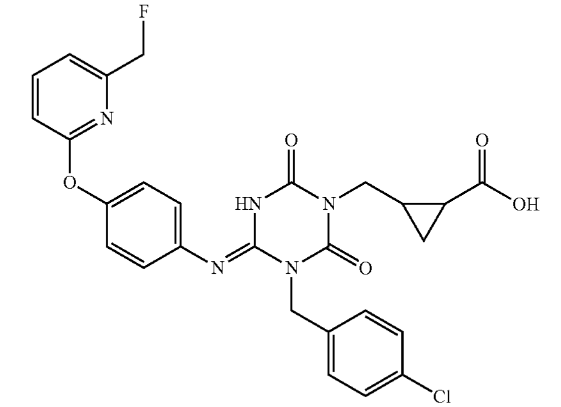 [SMILES: O=C(O)C1CC1Cn1c(=O)[nH]/c(=N\c2ccc(Oc3cccc(CF)n3)cc2)n(Cc2ccc(Cl)cc2)c1=O]
In some embodiments, the compound of formula (I) is a compound selected from those in Table 2:

TABLE 2

| | |
|---|---|
| (±) cis-2-((3-(4-chlorobenzyl)-2,6-dioxo-4-(4-(pyridin-2-yloxy)phenylimino)-1,3,5-triazin-1-yl)methyl)cyclopropanecarboxylic acid | (±) trans-2-((3-(4-chlorobenzyl)-2,6-dioxo-4-(4-(pyridin-2-yloxy)phenylimino)-1,3,5-triazin-1-yl)methyl)cyclopropanecarboxylic acid |
| (±)cis-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid |
| (±)cis-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid | (±)trans-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid |
| (±)cis-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid |
| (±)cis-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid |
| (±)cis-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid |
| (±)cis-2-((3-(4-chlorobenzyl)-4-((4-((3-fluoropyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((3-fluoropyridin-2-yl)oxy)phenyl)imino)-2,6-dioxo-1,3,5-triazin-1-yl)methyl)cyclopropan-1-carboxylic acid |
| (±)cis-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid | (±)trans-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid |

In some embodiments, the compound of formula (I) is a compound selected from those in

TABLE 3

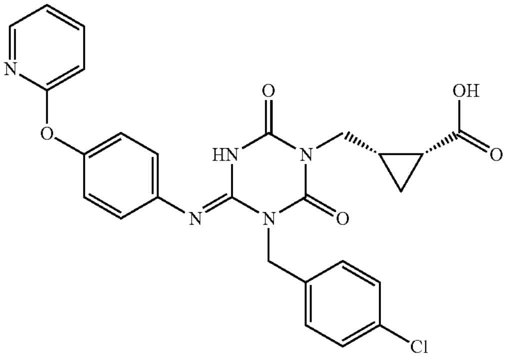 [SMILES: O=C(O)[C@@H]1C[C@@H]1Cn1c(=O)[nH]/c(=N\c2ccc(Oc3ccccn3)cc2)n(Cc2ccc(Cl)cc2)c1=O]

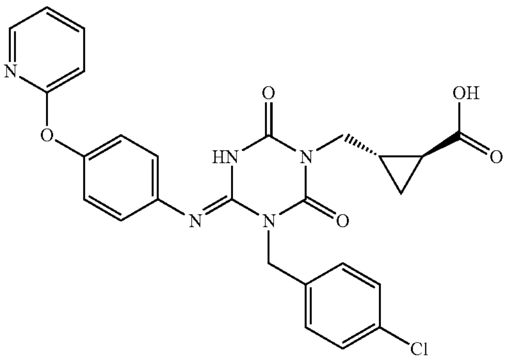 [SMILES: O=C(O)[C@H]1C[C@@H]1Cn1c(=O)[nH]/c(=N\c2ccc(Oc3ccccn3)cc2)n(Cc2ccc(Cl)cc2)c1=O]

TABLE 3-continued

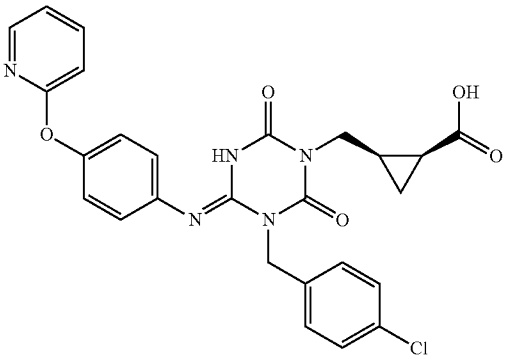 [SMILES: O=C(O)[C@H]1C[C@H]1Cn1c(=O)[nH]/c(=N\c2ccc(Oc3ccccn3)cc2)n(Cc2ccc(Cl)cc2)c1=O]

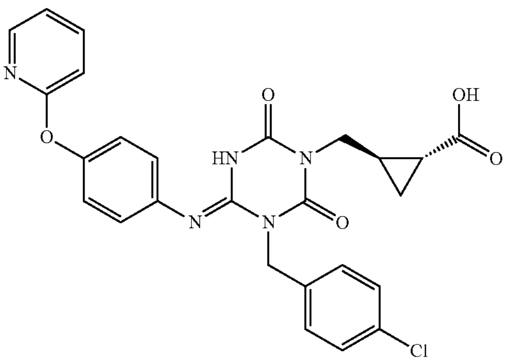 [SMILES: O=C(O)[C@@H]1C[C@H]1Cn1c(=O)[nH]/c(=N\c2ccc(Oc3ccccn3)cc2)n(Cc2ccc(Cl)cc2)c1=O]

TABLE 3-continued
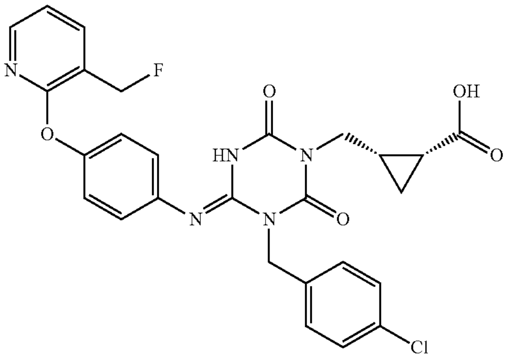
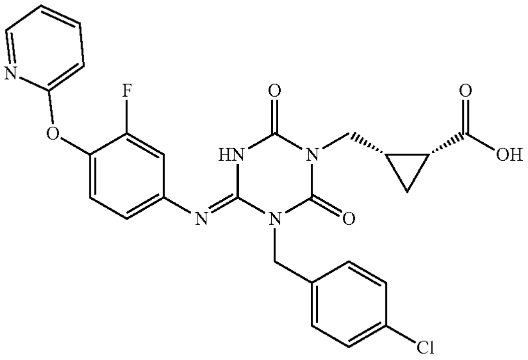
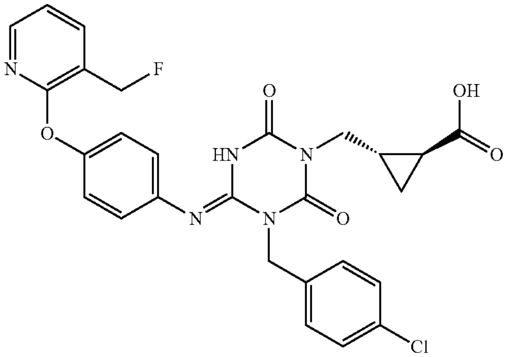 [SMILES: O=C(O)[C@H]1C[C@@H]1Cn1c(=O)[nH]/c(=N\c2ccc(Oc3ncccc3CF)cc2)n(Cc2ccc(Cl)cc2)c1=O]
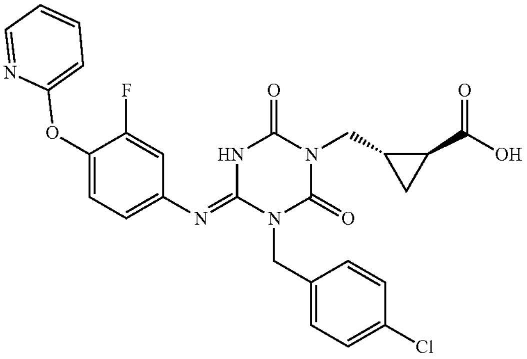
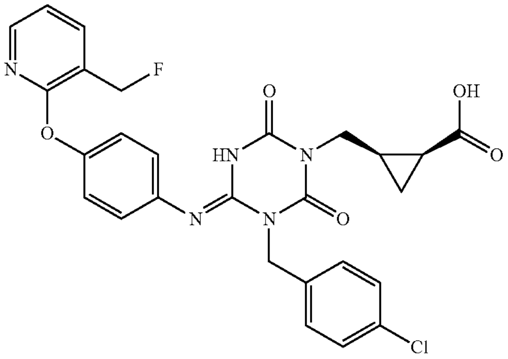 [SMILES: O=C(O)[C@H]1C[C@H]1Cn1c(=O)[nH]/c(=N\c2ccc(Oc3ncccc3CF)cc2)n(Cc2ccc(Cl)cc2)c1=O]
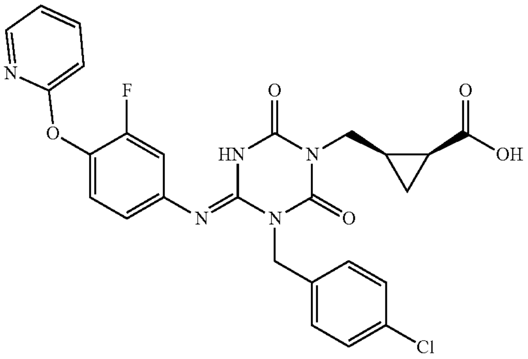
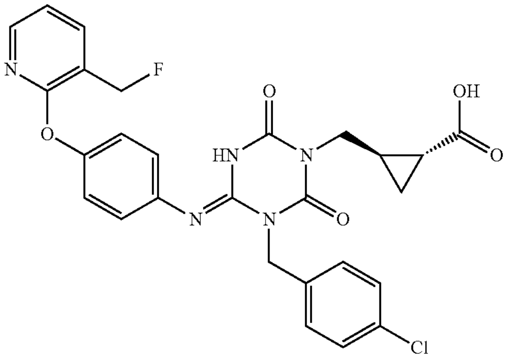 [SMILES: O=C(O)[C@@H]1C[C@H]1Cn1c(=O)[nH]/c(=N\c2ccc(Oc3ncccc3CF)cc2)n(Cc2ccc(Cl)cc2)c1=O]
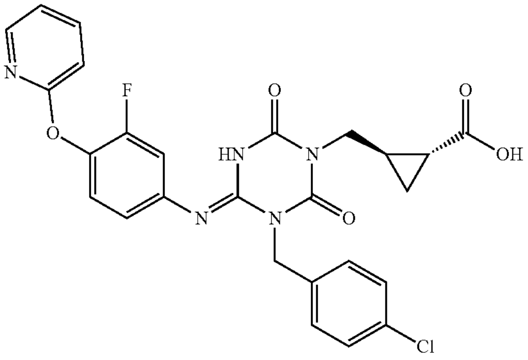 [SMILES: O=C(O)[C@@H]1C[C@H]1Cn1c(=O)[nH]/c(=N\c2ccc(Oc3ccccn3)c(F)c2)n(Cc2ccc(Cl)cc2)c1=O]
TABLE 3-continued TABLE 3-continued
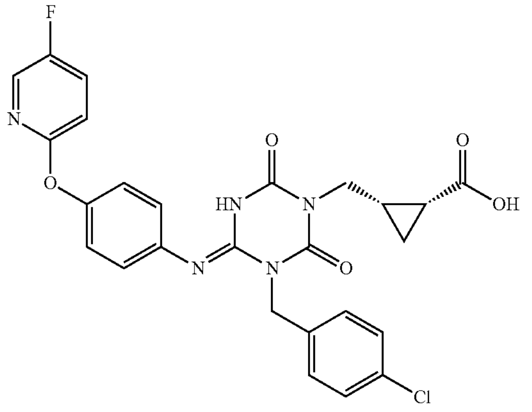 [SMILES: O=C(O)[C@@H]1C[C@@H]1Cn1c(=O)[nH]/c(=N\c2ccc(Oc3ccc(F)cn3)cc2)n(Cc2ccc(Cl)cc2)c1=O]
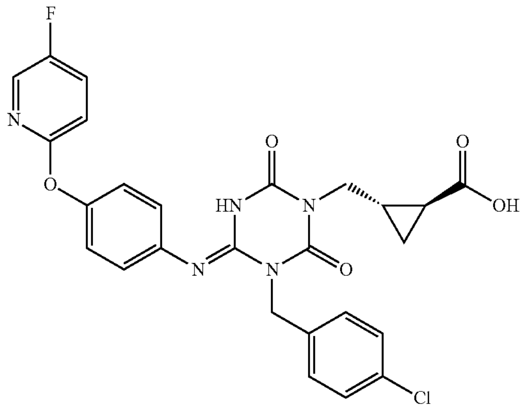 [SMILES: O=C(O)[C@H]1C[C@@H]1Cn1c(=O)[nH]/c(=N\c2ccc(Oc3ccc(F)cn3)cc2)n(Cc2ccc(Cl)cc2)c1=O]
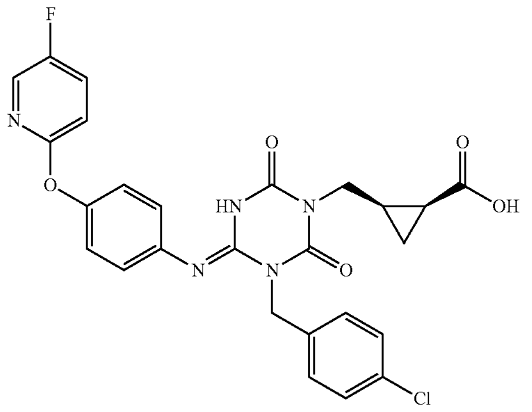 [SMILES: O=C(O)[C@H]1C[C@H]1Cn1c(=O)[nH]/c(=N\c2ccc(Oc3ccc(F)cn3)cc2)n(Cc2ccc(Cl)cc2)c1=O]
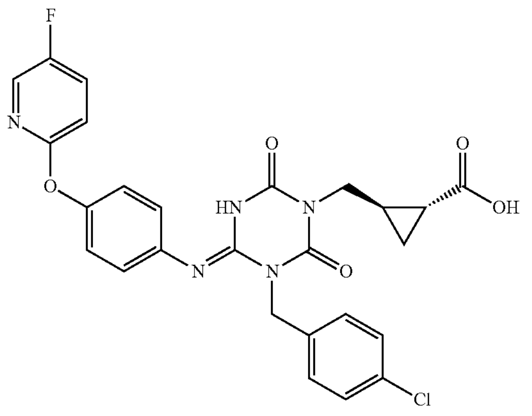 [SMILES: O=C(O)[C@@H]1C[C@H]1Cn1c(=O)[nH]/c(=N\c2ccc(Oc3ccc(F)cn3)cc2)n(Cc2ccc(Cl)cc2)c1=O]
TABLE 3-continued
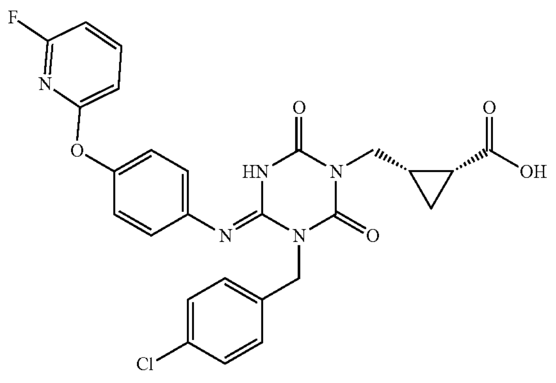 [SMILES: O=C(O)[C@@H]1C[C@@H]1Cn1c(=O)[nH]/c(=N\c2ccc(Oc3cccc(F)n3)cc2)n(Cc2ccc(Cl)cc2)c1=O]
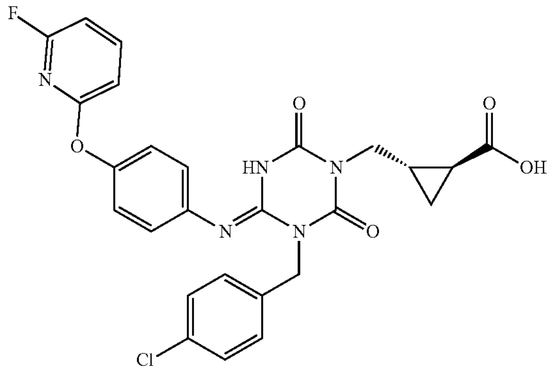 [SMILES: O=C(O)[C@H]1C[C@@H]1Cn1c(=O)[nH]/c(=N\c2ccc(Oc3cccc(F)n3)cc2)n(Cc2ccc(Cl)cc2)c1=O]
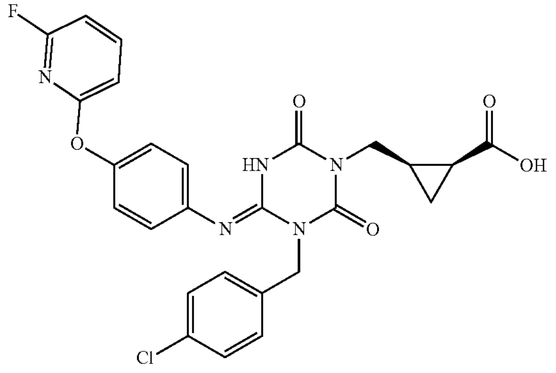 [SMILES: O=C(O)[C@H]1C[C@H]1Cn1c(=O)[nH]/c(=N\c2ccc(Oc3cccc(F)n3)cc2)n(Cc2ccc(Cl)cc2)c1=O]
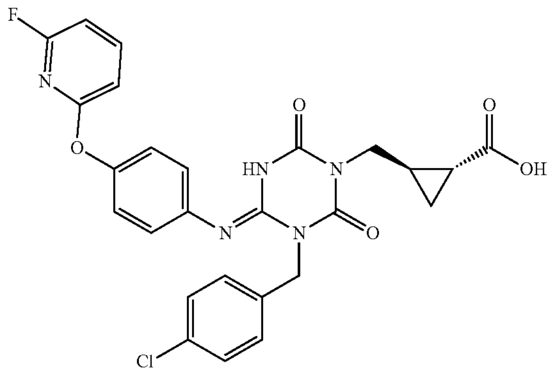 [SMILES: O=C(O)[C@@H]1C[C@H]1Cn1c(=O)[nH]/c(=N\c2ccc(Oc3cccc(F)n3)cc2)n(Cc2ccc(Cl)cc2)c1=O]

TABLE 3-continued
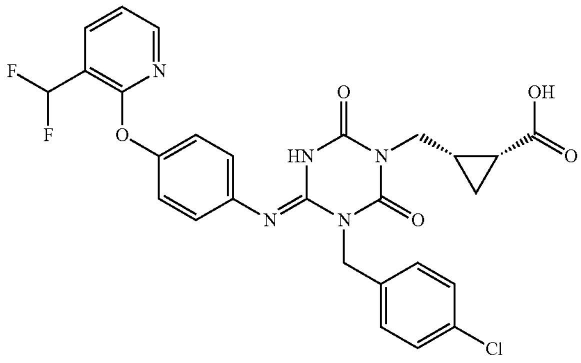 [SMILES: O=C(O)[C@@H]1C[C@@H]1Cn1c(=O)[nH]/c(=N\c2ccc(Oc3ncccc3C(F)F)cc2)n(Cc2ccc(Cl)cc2)c1=O]
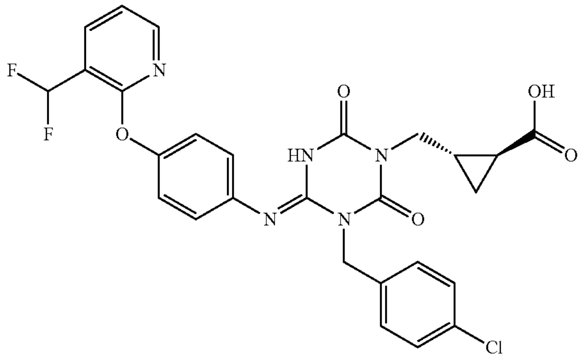 [SMILES: O=C(O)[C@H]1C[C@@H]1Cn1c(=O)[nH]/c(=N\c2ccc(Oc3ncccc3C(F)F)cc2)n(Cc2ccc(Cl)cc2)c1=O]
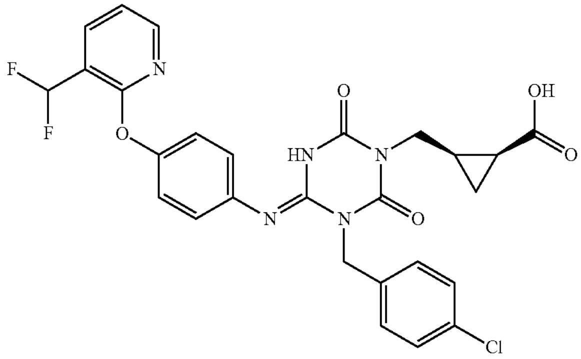 [SMILES: O=C(O)[C@H]1C[C@H]1Cn1c(=O)[nH]/c(=N\c2ccc(Oc3ncccc3C(F)F)cc2)n(Cc2ccc(Cl)cc2)c1=O]
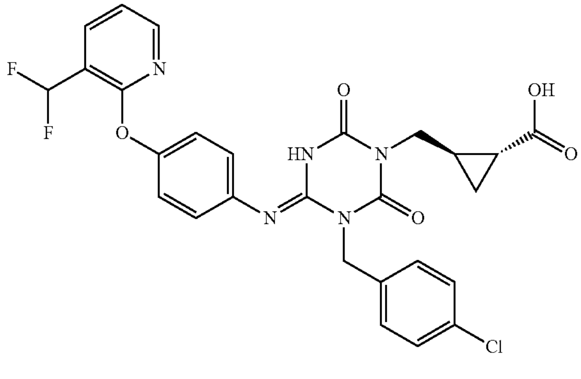 [SMILES: O=C(O)[C@@H]1C[C@H]1Cn1c(=O)[nH]/c(=N\c2ccc(Oc3ncccc3C(F)F)cc2)n(Cc2ccc(Cl)cc2)c1=O]
TABLE 3-continued
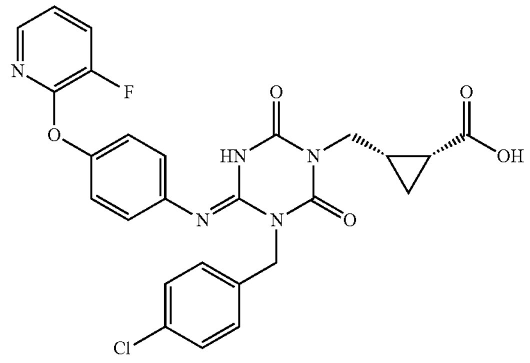 [SMILES: O=C(O)[C@@H]1C[C@@H]1Cn1c(=O)[nH]/c(=N\c2ccc(Oc3ncccc3F)cc2)n(Cc2ccc(Cl)cc2)c1=O]
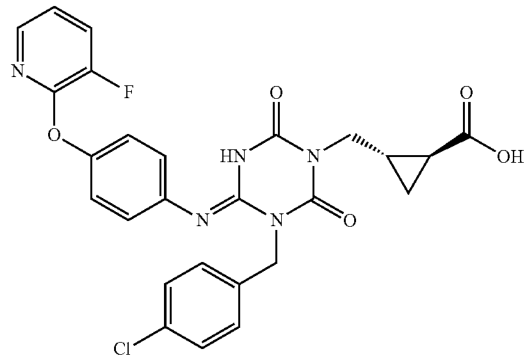 [SMILES: O=C(O)[C@H]1C[C@@H]1Cn1c(=O)[nH]/c(=N\c2ccc(Oc3ncccc3F)cc2)n(Cc2ccc(Cl)cc2)c1=O]
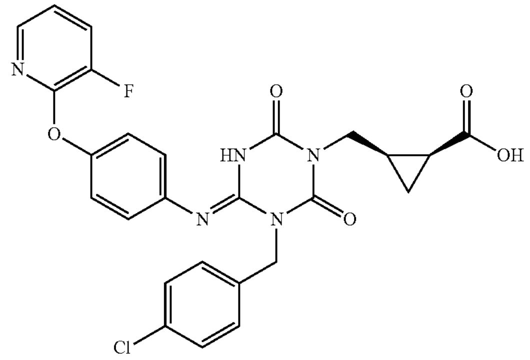 [SMILES: O=C(O)[C@H]1C[C@H]1Cn1c(=O)[nH]/c(=N\c2ccc(Oc3ncccc3F)cc2)n(Cc2ccc(Cl)cc2)c1=O]
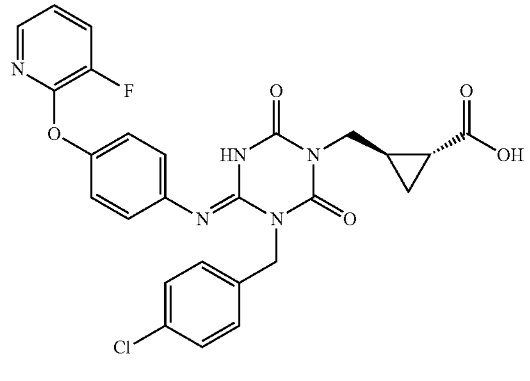 [SMILES: O=C(O)[C@@H]1C[C@H]1Cn1c(=O)[nH]/c(=N\c2ccc(Oc3ncccc3F)cc2)n(Cc2ccc(Cl)cc2)c1=O]

TABLE 3-continued

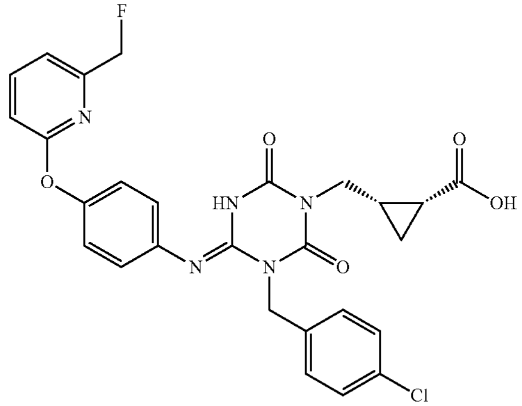 [SMILES: O=C(O)[C@@H]1C[C@@H]1Cn1c(=O)[nH]/c(=N\c2ccc(Oc3cccc(CF)n3)cc2)n(Cc2ccc(Cl)cc2)c1=O]

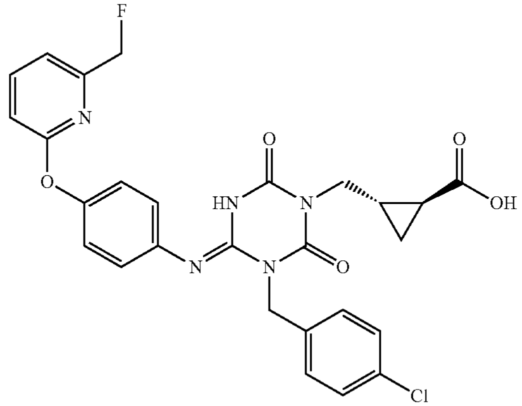 [SMILES: O=C(O)[C@H]1C[C@@H]1Cn1c(=O)[nH]/c(=N\c2ccc(Oc3cccc(CF)n3)cc2)n(Cc2ccc(Cl)cc2)c1=O]

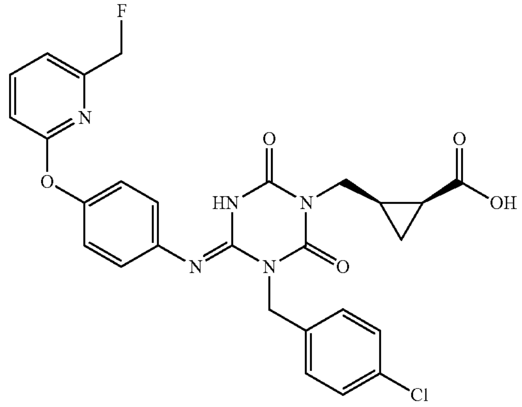 [SMILES: O=C(O)[C@H]1C[C@H]1Cn1c(=O)[nH]/c(=N\c2ccc(Oc3cccc(CF)n3)cc2)n(Cc2ccc(Cl)cc2)c1=O]

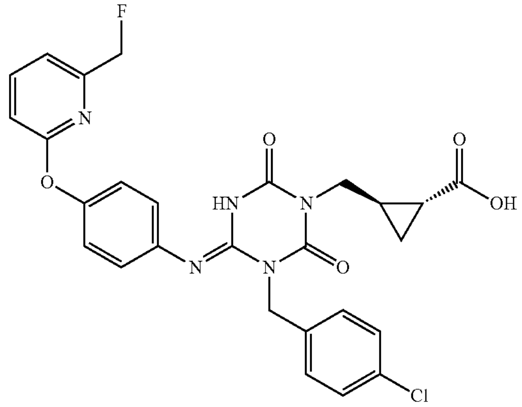 [SMILES: O=C(O)[C@@H]1C[C@H]1Cn1c(=O)[nH]/c(=N\c2ccc(Oc3cccc(CF)n3)cc2)n(Cc2ccc(Cl)cc2)c1=O]

A second aspect of the application provides a pharmaceutical composition comprising a compound represented by formula (I) above, or a pharmaceutically acceptable salt thereof, or a stereoisomer thereof, and a pharmaceutically acceptable carrier.

A third aspect of the application provides use of a compound represented by formula (I) above, or a pharmaceutically acceptable salt thereof, or a stereoisomer thereof in the preparation of a medicament for treatment of a disease associated with P2X3 activity or with P2X2/3 activity.

A fourth aspect of the application provides use of the pharmaceutical composition according to the second aspect in the preparation of a medicament for treatment of a disease associated with P2X3 activity or with P2X2/3 activity.

A fifth aspect of the application provides a method for treating a disease associated with P2X3 activity or with P2X2/3 activity comprising administering to a patient a therapeutic effective amount of the compound, or a pharmaceutically acceptable salt thereof, or a stereoisomer thereof according to the first aspect of the application, or the composition according to the second aspect of the application.

In some embodiments, the disease associated with P2X3 activity or with P2X2/3 activity is pain, a urinary tract disorder, a gastrointestinal disorder, cancer, an immune-related disease, cough, depression, anxiety, or a stress-related disorder. Further, the disease associated with P2X3 activity or with P2X2/3 activity is P2X3 or P2X2/3 mediated pain, urinary tract disorder, gastrointestinal disorder, cancer, immune-related disease, cough, depression, anxiety, or stress-related disorder.

BRIEF DESCRIPTION OF THE DRAWINGS

in FIG. 2,*and *** respectively indicate $P<0.05$ and $P<0.001$ for the compound group to be tested compared with the solvent group.

in FIG. 3, ** indicates $P<0.01$ for the compound group to be tested compared with the solvent group.

DETAILED DESCRIPTION

Figure 1:
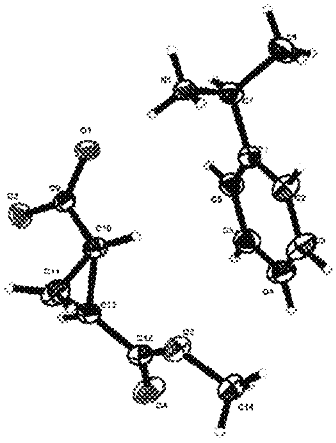
FIG. 1 shows the single crystal structure of the carboxylate of intermediate V7.

After extensive and in-depth research, the inventor unexpectedly found that these triazinylmethylcycloalkylcarboxylic acid derivatives have significant P2X3 inhibitory activity and low P2X2/3 inhibitory activity, and have a large safety window. This family of compounds is therefore expected to be developed as a medicament for treating various diseases mediated by P2X3 and/or P2X2/3 (or otherwise associated with P2X3 and/or P2X2/3) by regulating P2X3 and/or P2X2/3, which have, including but not limited to, good analgesic effects. Further, the inventor also found that in the triazinylmethylcycloalkylcarboxylic acid derivatives, there are obvious differences in activity between different stereoisomers.

On this basis, the inventor has completed the application.

DEFINITION OF TERMS

In order to enable a clearer understanding of the technical content of the present application, the terms of the present application are further described below.

"Alkyl" refers to linear and branched saturated aliphatic hydrocarbon groups. "$C_{1-8}$ alkyl" refers to alkyl having 1 to 8 carbon atoms, preferably $C_{1-6}$ alkyl, more preferably $C_{1-3}$ alkyl. Non-limiting examples of alkyl include: methyl, ethyl, n-propyl, iso-propyl, n-butyl, iso-butyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof.

"Cycloalkyl" and "cycloalkyl ring" are used interchangeably to refer to a saturated monocyclic, bicyclic, or polycyclic cyclic hydrocarbon group, which may be fused with aryl or heteroaryl. The cycloalkyl ring may optionally be substituted. In some embodiments, the cycloalkyl ring contains one or more carbonyls, e.g., a group containing oxo. "$C_{3-8}$ cycloalkyl" refers to monocyclic cycloalkyl having 3 to 8 carbon atoms. Non-limiting examples of cycloalkyl include cyclopropyl, cyclobutyl, cyclopentyl, cyclohexyl, cycloheptyl, cyclooctyl, cyclobutanone, cyclopentanone, cyclopentan-1,3-dione, and the like. $C_{3-6}$ cycloalkyl, including cyclopropyl, cyclobutyl, cyclopentyl and cyclohexyl, is preferred.

"Heterocycloalkyl" and "heterocycloalkyl ring" can be used interchangeably to refer to cycloalkyl comprising at least one heteroatom selected from the group consisting of nitrogen, oxygen and sulphur, which may be fused with aryl or heteroaryl. The heterocycloalkyl ring may optionally be substituted. In some embodiments, the heterocycloalkyl ring contains one or more carbonyls or thiocarbonyls, e.g., a group containing oxo or thio. "3- to 6-membered heterocycloalkyl" refers to monocyclic cyclic hydrocarbon group having 3 to 6 ring atoms, wherein 1, 2 or 3 ring atoms are heteroatoms selected from the group consisting of nitrogen, oxygen and sulfur. Preferably, 1 or 2 ring atoms in 3- to 6-membered heterocycloalkyl are heteroatoms selected from the group consisting of nitrogen, oxygen and sulfur. Non-limiting examples of monocyclic heterocycloalkyl include aziridinyl, oxiranyl, azetidinyl, oxetanyl, tetrahydrofuranyl, tetrahydrothienyl, tetrahydropyrrolyl, oxazolidinyl, dioxolanyl, piperidinyl, piperazinyl, morpholinyl, dioxanyl, thiomorpholinyl, thiomorpholin-1,1-dioxide, tetrahydropyranyl, azetidin-2-carbonyl, oxetan-2-carbonyl, dihydrofuran-2(3H)-carbonyl, pyrrolidin-2-carbonyl, pyrrolidin-2,5-dicarbonyl, dihydrofuran-2,5-dicarbonyl, piperidin-2-carbonyl, tetrahydro-2H-pyran-2-carbonyl, piperazin-2-carbonyl, morpholin-3-carbonyl, and the like.

"Heteroaryl" and "heteroaryl ring" can be used interchangeably to refer to a group of a monocyclic, bicyclic, or polycyclic 4n+2 aryl ring system having cyclic carbon atom and cyclic heteroatom (e.g., having 6 or 10 π-electrons shared in a cyclic arrangement), wherein each heteroatom is independently selected from the group consisting of nitrogen, oxygen and sulfur. In the present application, heterayl also includes a ring system in which the above heteraryl ring is fused with one or more cycloalkyl rings, heterocycloalkyl rings, cycloalkenyl rings, heterocycloalkenyl rings or aromatic rings. The heteroaryl ring may optionally be substituted. "5- to 6-membered heteroaryl" refers to monocyclic heteroaryl having 5 to 6 ring atoms, wherein 1, 2, 3 or 4 ring atoms are heteroatoms. Non-limiting examples include thienyl, furanyl, thiazolyl, isothiazolyl, imidazolyl, oxazolyl, pyrrolyl, pyrazolyl, triazolyl, 1,2,3-triazolyl, 1,2,4-triazolyl, 1,2,5-triazolyl, 1,3,4-triazolyl, tetrazolyl, isoxazolyl, oxadiazolyl, 1,2,3-oxadiazolyl, 1,2,4-oxadiazolyl, 1,2,5-oxadiazolyl, 1,3,4-oxadiazolyl, thiadiazolyl, pyridinyl, pyridazinyl, pyrimidinyl, pyrazinyl, triazinyl, and tetrazinyl. "Heteroatom" refers to nitrogen, oxygen or sulfur. For heteroaryl containing one or more nitrogen atoms, the linkage position may be a carbon or nitrogen atom, as long as the valency allows. A heteroaryl bicyclic system may include one or more heteroatoms in one or both rings.

"Halogen" refers to fluorine, chlorine, bromine or iodine.

"Halo" refers to halogen that substitutes for one or more (e.g., 1, 2, 3, 4 or 5) hydrogens in the group.

"Haloalkyl" refers to alkyl substituted by one or more (e.g., 1, 2, 3, 4 or 5) halogen atoms, and is preferably halo-$C_{1-8}$ alkyl, more preferably halo-$C_{1-6}$ alkyl, and more preferably halo-$C_{1-3}$ alkyl, wherein alkyl is as defined above. Examples of haloalkyl include (but are not limited to) monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl and the like.

"Deuteroalkyl" refers to alkyl substituted by one or more (e.g., 1, 2, 3, 4 or 5) deuterium atoms, preferably deutero-$C_{1-8}$ alkyl, more preferably deutero-$C_{1-6}$ alkyl, and more preferably deutero-$C_{1-3}$ alkyl, wherein alkyl is as defined above. Examples of deuteroalkyl include (but are not limited to) monodeuteromethyl, monodeuteroethyl, dideuteromethyl, dideuteroethyl, trideuteromethyl, trideuteroethyl and the like.

"Alkoxy" refers to —O-alkyl, preferably $C_{1-8}$ alkoxy, more preferably $C_{1-6}$ alkoxy, and most preferably $C_{1-3}$ alkoxy, wherein alkyl is as defined above. Non-limiting examples of alkoxy include methoxy, ethoxy, n-propoxy, isopropoxy, butoxy, tert-butoxy, isobutoxy, pentoxy and the like.

"Cycloalkyloxy" refers to —O-cycloalkyl, preferably $C_{3-8}$ cycloalkyloxy, and more preferably $C_{3-6}$ cycloalkyloxy, wherein cycloalkyl is as defined above. Non-limiting examples of cycloalkyloxy include cyclopropyloxy, cyclobutoxy, cyclopentyloxy, cyclohexyloxy and the like.

"Haloalkoxy" refers to alkoxy substituted by one or more (e.g., 1, 2, 3, 4 or 5) halogen atoms, preferably halo-$C_{1-8}$ alkoxy, more preferably halo-$C_{1-6}$ alkoxy, and more preferably halo-$C_{1-3}$ alkoxy, wherein alkoxy is as defined above. Haloalkoxy includes (but is not limited to) trifluoromethoxy, trifluoroethoxy, monofluoromethoxy, monofluoroethoxy, difluoromethoxy, difluoroethoxy and the like.

"Amino" refers to $—NH_2$. "Cyano" refers to —CN. "Nitro" refers to $—NO_2$. "Phenylmethyl" refers to $—CH_2$-phenyl. "Oxo" refers to =O. "Carboxyl" refers to —C(O)OH. "Acetyl" refers to $—C(O)CH_3$. "Hydroxymethyl" refers to $—CH_2OH$. "Hydroxyethyl" refers to $—CH_2CH_2OH$ or $—CHOHCH_3$. "Hydroxyl" refers to —OH. "Thiol" refers to —SH.

"Substituted" refers to a group, in which one or more hydrogen atoms, preferably 1 to 5 hydrogen atoms are each independently substituted by a corresponding number of substituents, and more preferably 1 to 3 hydrogen atoms are each independently substituted by a corresponding number of substituents. It is self-evident that the substituents are only in their possible chemical positions and that those skilled in the art are able to determine (experimentally or theoretically) possible or impossible substitutions without undue effort. For example, amino or hydroxyl having a free hydrogen may be unstable when combined with a carbon atom having an unsaturated (e.g., olefinic) bond.

When the number of substituents is not specified in the application, it means that an optional number of substituents can be used for substitution.

Unless otherwise defined, "substituents each independently selected from the group consisting of . . . " in the present application refers to a group with more than one hydrogens substituted by substituents, and the substituents can be of identical or different types, and the selected substituents are each of independent type.

Unless otherwise defined, any group herein may be substituted or unsubstituted. When the above groups are substituted, the substituents are preferably 1 to 5 groups each independently selected from the group consisting of deuterium, halogen (preferably fluorine or chlorine), cyano, hydroxyl, carboxyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), $C_{2-4}$ alkenyl, $C_{2-4}$ alkynyl, halo-$C_{1-8}$ alkyl (preferably halo-$C_{1-6}$ alkyl, more preferably halo-$C_{1-3}$ alkyl), cyano-substituted $C_{1-8}$ alkyl (preferably cyano-substituted $C_{1-6}$ alkyl, more preferably cyano-substituted $C_{1-3}$ alkyl), halo-$C_{1-8}$ alkoxy (preferably halo-$C_{1-6}$ alkoxy, more preferably halo-$C_{1-3}$ alkoxy), $NR_{a0}R_{b0}$, —$SO_2C_{1-3}$ alkyl, —$S(O)C_{1-3}$ alkyl, —$C(O)NR_{a1}R_{b1}$, —$C(O)C_{1-8}$ alkyl (preferably —$C(O)C_{1-6}$ alkyl, more preferably —$C(O)C_{1-3}$ alkyl), —$C(O)OC_{1-8}$ alkyl (preferably —$C(O)OC_{1-6}$ alkyl, more preferably —$C(O)OC_{1-3}$ alkyl), —$OC(O)C_{1-8}$ alkyl (preferably —$OC(O)C_{1-6}$ alkyl, more preferably —$OC(O)C_{1-3}$ alkyl), $C_{3-6}$ cycloalkyl, $C_{3-6}$ cycloalkyloxy, 3- to 6-membered heterocycloalkyl, phenyl, and 5- to 6-membered heteroaryl; wherein, among the substituents, the 3- to 6-membered heterocycloalkyl, phenyl, and 5- to 6-membered heteroaryl are unsubstituted or substituted by 1, 2, or 3 substituents each independently selected from the group consisting of halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkyloxy, 3- to 6-membered heterocycloalkyl, phenyl, and 5- to 6-membered heteroaryl;

$R_{a1}$ and $R_{b1}$ are each independently hydrogen or $C_{1-3}$ alkyl; or $R_{a1}$, $R_{b1}$ and the linked nitrogen atom together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —$S(O)C_{1-3}$ alkyl, —$C(O)NH_2$, —$C(O)NH(C_{1-3}$ alkyl), —$C(O)N(C_{1-3}$ alkyl$)_2$, —$C(O)OC_{1-3}$ alkyl, —$OC(O)C_{1-3}$ alkyl, $C_{3-6}$ cycloalkyl, $C_{3-6}$ cycloalkyloxy, and 3- to -6-membered heterocycloalkyl; and $R_{a0}$ and $R_{b0}$ are each independently hydrogen, $C_{1-3}$ alkyl, or acetyl; or $R_{a0}$, $R_{b0}$ and nitrogen atom linked to $R_{a0}$ and $R_{b0}$ together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —$S(O)C_{1-3}$ alkyl, —$C(O)NH_2$, —$C(O)NH(C_{1-3}$ alkyl), —$C(O)N(C_{1-3}$ alkyl$)_2$, —$C(O)OC_{1-3}$ alkyl, —$OC(O)C_{1-3}$ alkyl, $C_{3-6}$ cycloalkyl, $C_{3-6}$ cycloalkyloxy, and 3- to -6-membered heterocycloalkyl.

In the present application, when two or more "preferably" appear in a scheme, any two "preferably" can be independent of each other.

In the present application, any two substituents may be identical or different when the number of substituents is greater than 1. For example, the two substituents can be two identical or different halogen atoms, or can be one halogen and one hydroxyl.

The various substituents mentioned above per se can also be substituted by the groups described therein.

Pharmaceutical Composition

Generally the compound of the present application, or the pharmaceutically acceptable salt thereof, or the stereoisomer thereof, can be administered in a suitable dosage form with one or more pharmaceutical carriers. These dosage forms are suitable for oral, rectal, topical, intraoral administration and other parenteral administration (e.g., subcutaneous, intramuscular, intravenous administration, and the like). For example, dosage forms suitable for oral administration include capsules, tablets, granules and syrups. The compound of the present application contained in these formulations may be solid powders or granules; solutions or suspensions in aqueous or non-aqueous liquids; water-in-oil or oil-in-water emulsions, and the like. The above dosage forms can be made from the active compound with one or more carriers or excipients by general pharmaceutical methods. The above carriers need to be compatible with the active compound or other excipients. For solid dosage forms, commonly used non-toxic carriers include, but are not limited to, mannitol, lactose, starch, magnesium stearate, cellulose, glucose, sucrose and the like. Carriers for liquid formulations include water, physiological saline, aqueous glucose solution, ethylene glycol, polyethylene glycol and the like. The active compound can be formed into a solution or a suspension with the above carriers.

"Pharmaceutically acceptable carrier" refers to a non-toxic, inert, solid, semi-solid material or liquid filler, diluent, encapsulant or adjuvant or excipient of any type, which is compatible with a patient, preferably a mammal, more preferably a human, and is suitable for delivery of the active reagent to a target without terminating the activity of the reagent.

The compositions of the present application are formulated, dosed and administered in a manner consistent with medical practice guideline. The "therapeutically effective amount" of the compound to be administered is determined by the specific disease to be treated, the individual to be treated, the cause of the disease, the target of the drug and the route of administration.

"Therapeutically effective amount" refers to the amount of the compound of the present application that will cause a biological or medical response in an individual, such as decreasing or inhibiting enzyme or protein activity or ameliorating a symptom, alleviating a condition, slowing or delaying a disease process or preventing a disease, etc.

The therapeutically effective amount of the compound of the present application, or a pharmaceutically acceptable salt thereof, or a stereoisomer thereof, contained in the pharmaceutical composition or the medicinal composition of the present application is preferably 0.1 mg/kg to 5 g/kg (body weight).

The term “patient” refers to an animal, preferably a mammal, and more preferably a human. The term “mammal” refers to a warm-blooded vertebrate mammal, including, for example, cats, dogs, rabbits, bears, foxes, wolves, monkeys, deer, mice, pigs and humans.

“Treatment” refers to alleviation, slowing of progression, attenuation, prevention, or maintenance of an existing disease or condition (e.g., cancer). Treatment also includes curing one or more symptoms of a disease or condition, preventing its development, or reducing it to a certain extent.

The “pharmaceutically acceptable salt” includes a pharmaceutically acceptable acid addition salt and a pharmaceutically acceptable base addition salt.

“Pharmaceutically acceptable acid addition salt” refers to a salt formed with an inorganic or organic acid, which is capable of retaining the biological effectiveness of the free base without other side effects.

“Pharmaceutically acceptable base addition salt” includes, but is not limited to, a salt of inorganic base and a salt of organic base.

The compound of the present application can contain one or more chiral centers, and can exist in different optically active forms. When the compound contains one chiral center, the compound includes enantiomers. Diastereomers can exist when the compound contains more than one chiral center. The present application includes the two stereoisomers of the compound and mixtures of the two stereoisomers, such as a racemate, a diastereomer mixture and the like.

In addition, the compound of formula (I) of the application may also include cis-trans isomers due to the existence of cycloalkyl structure, wherein the possibly existed asymmetric carbon atom(s) of the compound of formula (I) can exist in the form of (R) configuration, (S) configuration, (R,R) configuration, (S,R) configuration, or (R,S) configuration. The present application includes cis-trans isomers and mixtures thereof, such as cis-isomer mixture, trans-isomer mixture, and the like.

In addition, compounds of formula (I) of the application also include tautomers, which refer to isomeric forms of compound in equilibrium with each other. It is readily understood by those skilled in the art that various functional groups and other structures may exhibit tautomeric forms, such as imine-enamine tautomers in the compound structure of the present application as follows, and the present application includes these tautomers and mixtures thereof.

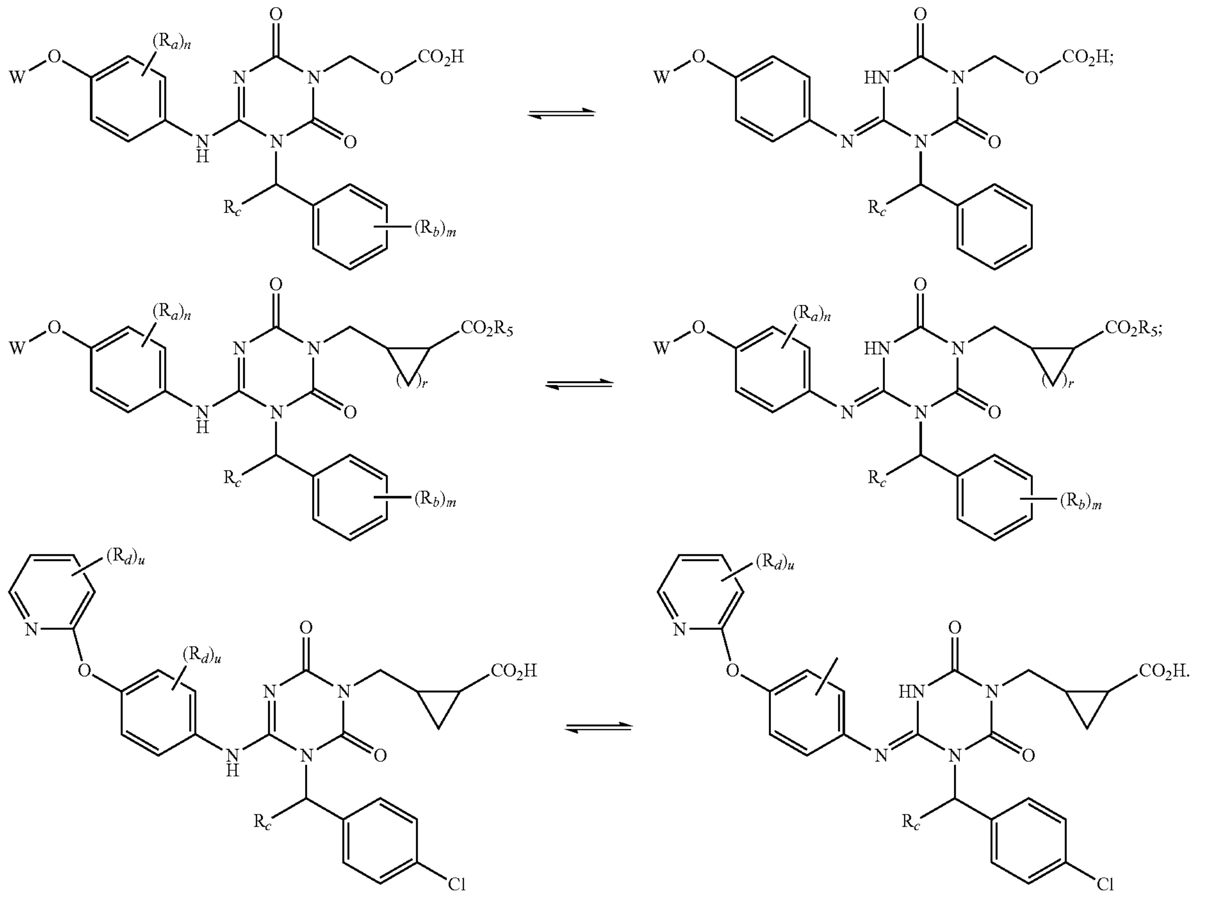

Enantiomers, diastereomers, cis-isomers, trans-isomers, imine-enamine tautomers, keto-enol tautomers and mixtures of these isomers of the compound of the application are within the protection scope of the application. Enantiomers, diastereomers, and cis-trans isomers can be separated by methods known in the art, such as crystallization and chiral chromatography.

Preparation Method

The present application provides preparation methods of the compound of formula (I), which can be synthesized using standard synthetic techniques known to those skilled in the art or using a combination of methods known in the art with the methods described in the present application. The solvents, temperatures and other reaction conditions given in the present application can be varied according to techniques in the art. The reactions described can be used sequentially to provide the compounds of the present application, or can be used to synthesize fragments that are subsequently incorporated by the methods described herein and/or methods known in the art.

The compounds described herein may be synthesized using methods similar to those described below or exemplary methods described in the examples, or relevant disclosures used by those skilled in the art, by using appropriate optional starting materials. The starting materials used to synthesize the compounds described herein may be synthesized or may be obtained from commercial sources. The compounds described herein and other related compounds having different substituents can be synthesized using techniques and raw materials known to those skilled in the art. General methods for preparing the compounds disclosed by the present application may be derived from reactions known in the art and the reactions may be modified in terms of reagents and conditions considered appropriate by those skilled in the art to introduce various moieties of the molecules provided by the present application.

Compared with the prior art, the main advantages of the application include: providing a series of structurally novel triazinylmethylcycloalkylcarboxylic acid derivatives, which have significantly high P2X3 inhibitory activity and low P2X2/3 inhibitory activity, have a large safety window, have the potential to be used in the treatment of a disease associated with P2X3 activity or with P2X2/3 activity, and have, including but not limited to, good analgesic effects. Further, in the triazinylmethylcycloalkylcarboxylic acid derivatives, there are obvious differences in activity between different stereoisomers.

The present application is further described below in conjunction with specific examples. It should be understood that these examples are used only to illustrate the application and are not intended to limit the scope of the application. Experimental methods for which specific conditions are not indicated in the following examples are generally in accordance with conventional conditions such as those described in Sambrook et al., Molecular Cloning: A Laboratory Manual (New York: Cold Spring Harbor Laboratory Press, 1989), or in accordance with conditions recommended by the manufacturer. Percentages and parts are by weight unless otherwise indicated. Unless otherwise defined, terms used herein have the same meaning as those familiar to those skilled in the art. In addition, any methods and materials similar or equivalent to what is recorded herein may be applied in the present application.

Reagent and Instrument $^1$HNMR: Bruker AVANCE-400 NMR spectrometer with tetramethylsilane (TMS) as internal standard.

LC-MS: Agilent 1290 HPLC System/6130/6150 MS LC-MS mass spectrometer (manufacturer: Agilent), column: Waters BEH/CHS, 50×2.1 mm, 1.7 m.

Preparative high performance liquid chromatography (pre-HPLC): GX-281 (manufacturer: Gilson).

ISCO Combiflash-Rf75 or Rf200 automatic column passing machine and Agela 4 g, 12 g, 20 g, 40 g, 80 g, and 120 g disposable silica gel column were used.

Known starting materials may be synthesized using or in accordance with methods known in the art, or may be purchased from companies such as ABCR GmbH&Co.KG, Acros Organics, Aldrich Chemical Company, Accela ChemBio Inc and Darui Chemicals, etc.

In examples, the reaction may be monitored by thin layer chromatography (TLC) and compound purification may be performed by column chromatography. The developing agent system used for column chromatography or TLC can be selected from the group consisting of: dichloromethane and methanol system, n-hexane and ethyl acetate system, petroleum ether and ethyl acetate system, acetone system, and the like. The volume ratio of solvents is adjusted according to the polarity of the compound.

As used herein, DCM is dichloromethane, DCE is 1,2-dichloroethane, DMF is N,N-dimethylformamide, DMSO is dimethyl sulfoxide, THE is tetrahydrofuran, EA is ethyl acetate, PE is petroleum ether, n-Buli is n-butyl lithium, HATU is 2-(7-azobenzotriazole)-N,N,N',N'-tetramethyluronium hexafluorophosphate, TEA is triethylamine, DIEA or DIPEA is N,N-diisopropylethylamine, NBS is n-bromosuccinimide, NCS is N-chlorosuccinimide, TBAF is tetrabutylammonium fluoride, and DEAD is diethyl azodicarboxylate.

As mentioned herein, the percentage content refers to the mass percentage for both solid-liquid mixing and solid-solid mixing, and to the volume percentage for liquid-liquid mixing, unless otherwise specified. All solvents are water, unless otherwise specified.

As used herein, room temperature refers to about 20° C. to 30° C.

As used herein, "overnight" refers to performing for about 10 hours to 16 hours.

Preparation of Intermediate V1

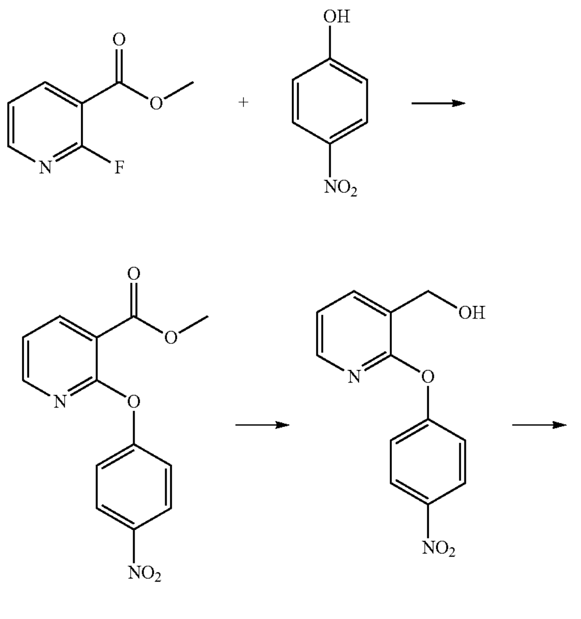

-continued

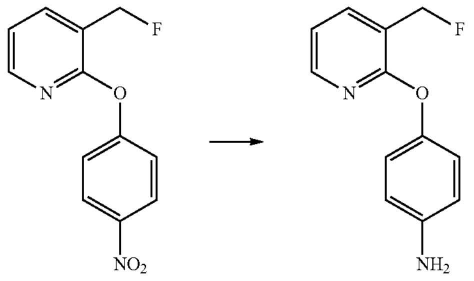

V1

Step 1: Methyl 2-fluoropyridin-3-carboxylate (557.57 mg, 3.59 mmol), 4-nitrophenol (500 mg, 3.59 mmol) and cesium carbonate (1.76 g, 5.39 mmol) were added to DMF (10 mL). The reaction solution was stirred at 80° C. for 16 hours. The reaction solution was filtered and concentrated under reduced pressure. The residue was purified by silica gel column chromatography with eluent system (petroleum ether/ethyl acetate: 1/0 to 1/1) to give methyl 2-(4-nitrophenoxy)nicotinate (650 mg). LC-MS m/z (ESI): 275.0 $[M+1]^+$.

Step 2: Methyl 2-(4-nitrophenoxy)nicotinate (470 mg, 1.71 mmol) was dissolved in THE (20 mL), and the resultant was cooled to −78° C. under argon protection. Then a solution of lithium aluminum hydride in THE (1 M, 2.57 mL) was added dropwise. The reaction solution was stirred at −78° C. for 1 hour. Sodium sulfate decahydrate was added to quench the reaction. The reaction solution was filtered and concentrated under reduced pressure. The residue was purified by silica gel column chromatography with eluent system (petroleum ether/ethyl acetate: 1/0 to 0/1) to give (2-(4-nitrophenoxy)pyridin-3-yl)methanol (405 mg). MS m/z (ESI): 247.0 $[M+1]^+$.

Step 3: (2-(4-nitrophenoxy)pyridin-3-yl)methanol (200 mg, 812.29 μmol) was dissolved in DCM (10 mL), and the resultant was cooled to 0° C. under argon protection. Then bis(2-methoxyethyl)aminosulphur trifluoride (539.13 mg, 2.44 mmol) was added dropwise. The reaction solution was naturally warmed up to room temperature and stirred for 5 hours. Saturated sodium bicarbonate solution (30 mL) was added. The resultant was extracted with DCM (30 mL×3). The organic phase was dried, filtered, and concentrated under reduced pressure. The residue was purified by silica gel column chromatography with eluent system (petroleum ether/ethyl acetate: 1/0 to 3/1) to give 3-(fluoromethyl)-2-(4-nitrophenoxy)pyridine (177 mg). MS m/z (ESI): 249.0 $[M+1]^+$.

Step 4: 3-(fluoromethyl)-2-(4-nitrophenoxy)pyridine (100 mg, 402.89 μmol), iron powder (112.50 mg, 2.01 mmol), and ammonium chloride (107.75 mg, 2.01 mmol) were added to a solvent mixture of methanol (2 mL), THE (2 mL) and water (2 mL). The reaction solution was stirred at 75° C. for 2 hours. The reaction solution was filtered and concentrated under reduced pressure. The residue was purified by silica gel column chromatography with eluent system (dichloromethane/methanol: 1/0 to 10/1) to give 4-(3-(fluoromethyl)pyridin-2-yloxy)aniline V1 (82 mg). MS m/z (ESI): 219.1 $[M+1]^+$.

Preparation of Intermediate V2

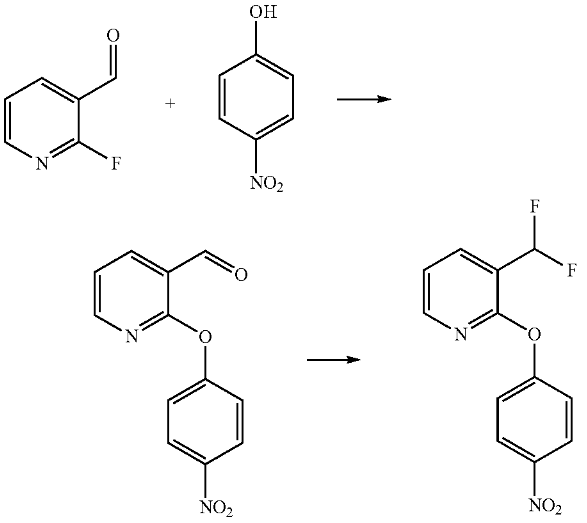

V2

Step 1: 2-fluoronicotinaldehyde (449.65 mg, 3.59 mmol), 4-nitrophenol (500 mg, 3.59 mmol) and cesium carbonate (1.76 g, 5.39 mmol) were added to DMF (10 mL). The reaction solution was stirred at 60° C. for 2 hours. The reaction solution was filtered and concentrated under reduced pressure. The residue was purified by silica gel column chromatography with eluent system (petroleum ether/ethyl acetate: 1/0 to 1/1) to give 2-(4-nitrophenoxy)nicotinaldehyde (450 mg). MS m/z (ESI): 244.9 $[M+1]^+$.

Step 2: 2-(4-nitrophenoxy)nicotinaldehyde (420 mg, 1.72 mmol) was dissolved in DCM (20 mL), and the resultant was cooled to 0° C. under argon protection. Then diethylaminosulfur trifluoride (1.39 g, 8.60 mmol) was added dropwise. The reaction solution was naturally warmed up to room temperature and stirred for 16 hours. 30 mL of saturated sodium bicarbonate solution was added. The resultant was extracted with DCM (30 mL×3). The organic phase was dried, filtered, and concentrated under reduced pressure. The residue was purified by silica gel column chromatography with eluent system (petroleum ether/ethyl acetate: 1/0 to 1/1) to give 3-(difluoromethyl)-2-(4-nitrophenoxy)pyridine V2 (405 mg). MS m/z (ESI): 267.0 $[M+1]^+$.

Preparation of Intermediate V3

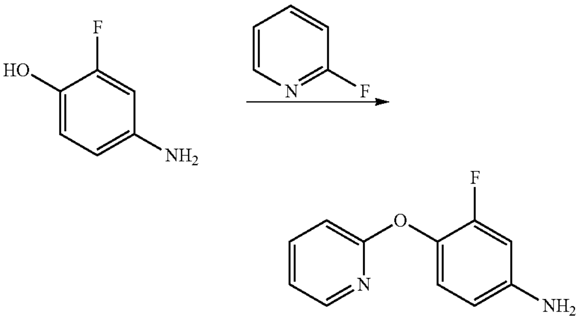

V3

4-amino-2-fluorophenol (1 g, 10.30 mmol) was dissolved in DMF (20 mL), to which cesium carbonate (6.71 g, 20.60 mmol) and 2-fluoropyridine (1.31 g, 10.30 mmol) were added. The reaction solution was stirred at 90° C. for 12 hours. The reaction solution was cooled to room temperature and was filtered. The filtrate was concentrated under reduced pressure. The residue was purified by silica gel column chromatography with eluent system (petroleum ether/ethyl acetate: 5/0 to 3/1) to give 3-fluoro-4-(pyridin-2-oxy)aniline V3 (1.5 g). MS m/z (ESI): 205.1 $[M+1]^+$.

Preparation of Intermediate V4

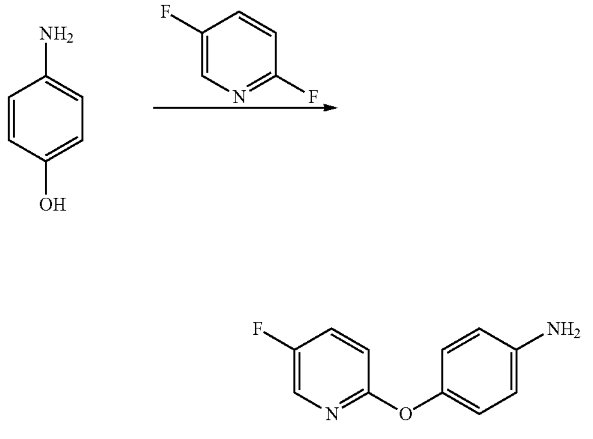

V4

2,5-difluoropyridine (4.4 g, 38.23 mmol) and 4-aminophenol (4.17 g, 38.23 mmol) were dissolved in DMF (50 mL), to which $Cs_2CO_3$ (13.70 g, 42.06 mmol) was added. The reaction system was stirred at 90° C. for 16 hours. The reaction solution was spin-dried under reduced pressure. The residue was purified by silica gel column chromatography (0 to 50% EA/PE) to give 4-((5-fluoropyridin-2-yl)oxy)aniline V4 (6 g). MS m/z (ESI): 204.6 $[M+1]^+$.

Preparation of Intermediate V5

V5

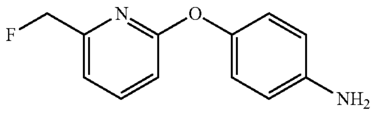

The intermediate V5 was obtained by using methyl 6-fluoropyridin-2-carboxylate as raw material and referring to the preparation method of the intermediate V1.

Preparation of methyl (±) trans-2-((3-(4-chlorobenzyl)-4-ethylthio-2,6-dioxo-3,6-dihydro-1,3,5-triazin-1(2H)-yl)methyl)cyclopropan-1-carboxylate (intermediate V6)

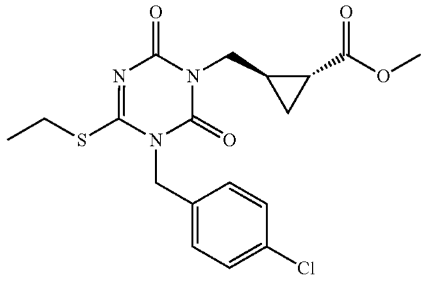

and

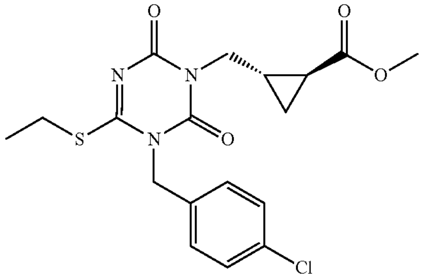

Step 1: Dimethyl (±) trans-1,2-cyclopropanedicarboxylate (25 g, 0.158 mol) was dissolved in a solvent mixture of methanol (90 mL)/water (10 mL). The solution was cooled in an ice bath. Sodium hydroxide (6.65 g, 0.166 mol) was added. The reaction solution was stirred overnight at room temperature. The reaction solution was then concentrated, diluted with 40 mL of water. The pH was adjusted to 6 with 3 M hydrochloric acid. The resultant was extracted with ethyl acetate. The combined organic phase was washed with saturated sodium chloride solution, dried with sodium sulfate, and concentrated to give (±) trans-2-(methoxycarbonyl)cyclopropan-1-carboxylic acid (22 g), MS m/z (ESI): 145.0 $[M+1]^+$.

Step 2: The (±) trans-2-(methoxycarbonyl)cyclopropan-1-carboxylic acid (22 g, 0.153 mol) was dissolved in dry THF (100 mL). A solution of borane in tetrahydrofuran (1 M, 183 mL, 0.183 mol) was added dropwise under ice bath cooling. The reaction solution was stirred at room temperature for 2 hours. Water was added to the reaction solution dropwise to quench the reaction. After no bubbles were formed, the reaction solution was filtered. The filtrate was concentrated. The residual was diluted with ethyl acetate, washed with water, washed with saturated sodium chloride solution, dried and concentrated to give methyl (±) trans-2-(hydroxymethyl)cyclopropan-1-carboxylate (20 g), MS m/z (ESI):131.1 $[M+1]^+$.

Step 3: methyl (±) trans-2-(hydroxymethyl)cyclopropan-1-carboxylate (7 g, 53.85 mmol), 1-(4-chlorobenzyl)-6-(ethylthio)-1,3,5-triazin-2,4(1H,3H)-dione (16 g, 53.85 mmol, CAS. NO. 1239691-22-5) and triphenylphosphine (22.6 g, 86.16 mmol) were suspended in dry dichloromethane. DEAD (15 g, 86.16 mmol) was added dropwise under ice bath cooling. The reaction solution was gradually clarified, and the reaction solution was concentrated after stirring at room temperature for 3 hours. The residue was diluted with 90 mL of ethyl acetate. Then 150 mL of petroleum ether was slowly added under stirring. A large amount of solid was precipitated. The solid was filtered. The filtrate was concentrated. The residue was purified by silica gel column chromatography (EA/PE=1/1.8) to give methyl (±) trans-2-((3-(4-chlorobenzyl)-4-ethylthio-2,6-dioxo-3,6-dihydro-1,3,5-triazin-1(2H)-yl)methyl)cyclopropan-1-carboxylate V6 (25 g), MS m/z (ESI): 410.1 $[M+1]^+$.

Preparation of methyl (1S,2S)-2-(hydroxymethyl)cyclopropan-1-carboxylate (Intermediate V7)

V7

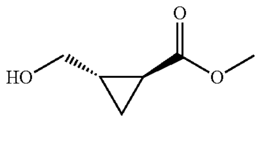

Step 1: (±) Trans-2-(methoxycarbonyl)cyclopropan-1-carboxylic acid (8.5 g) and (S)-alpha-methylbenzylamine (7.86 g) was added to toluene (85 mL). The reaction solution was stirred at 50° C. for 1 hour, and was then spin-dried. 85 mL of methyl tert-butyl ether was added. The mixture was stirred, filtered, and dried to give 13.5 g of a solid. 5.0 g of the solid was added to 50 mL of acetone. It was dissolved and clarified under reflux. The solution was stirred for 0.5 hour, cooled down naturally, stirred at room temperature for another 2 hour, and filtered. 1.4 g of a white solid was obtained. The white solid was stirred under reflux in 21 mL of acetone for 1 hour. The solution was cooled to room temperature and filtered to give a solid (800 mg, ee>99.0%). 100 mg of the solid was dissolved in 1 mL of acetone. The solution was slowly volatilized. A colorless crystal was precipitated. The absolute configuration of the crystal was confirmed to be (1S,2S) by single crystal X-ray analysis with Bruker D8 venture X-ray single crystal diffractometer. The structure diagram is shown in FIG. 1. Therefore, the absolute configuration of the intermediate V7 can be inferred from the single crystal structure of the carboxylate as (1S,2S) configuration.

Instrument Parameters:

| | |
|---|---|
| Light source: Mo target | Current voltage: 50 kV, 1.4 mA |
| X-ray: Mo—K α (λ = 0.71032 Å) | Exposure time: 3 s |
| Detector: CMOS surface detector | Distance from surface detector to sample: 50 mm |
| Resolution: 0.80 Å | Test temperature: 170(2) K |

Step 2: The carboxylate (700 mg) was dissolved in 5 mL of water, to which 5 mL of 10% wt potassium bisulphate solution was then added. The aqueous solution was extracted twice with 10 mL of methyl tert-butyl ether. The organic phases were combined and spin-dried to give (1S,2S)-2-(methoxycarbonyl)cyclopropan-1-carboxylic acid (300 mg).

Step 3: (1S,2S)-2-(methoxycarbonyl)cyclopropan-1-carboxylic acid (300 mg) was dissolved in 1 mL of tetrahydrofuran, to which a solution of borane in tetrahydrofuran (1 mol/L, 10.4 mL) was added dropwise under an ice bath. After the addition, the reaction solution was warmed up to room temperature and stirred for 5 hours. The reaction solution was quenched with 10 mL of methanol under an ice bath and spin-dried. 10 mL of water was added. The mixture was extracted with methyl tert-butyl ether (10 mL×3). The organic phases were combined and washed once with 10 mL of water. The resultant was dried, filtered and spin-dried to give methyl (1S,2S)-2-(hydroxymethyl)cyclopropan-1-carboxylate V7 (250 mg).

Example 1: Preparation of (±) cis-2-((3-(4-chlorobenzyl)-2,6-dioxo-4-(4-(pyridin-2-yloxy)phenylimino)-1,3,5-triazin-1-yl)methyl)cyclopropanecarboxylic acid H1

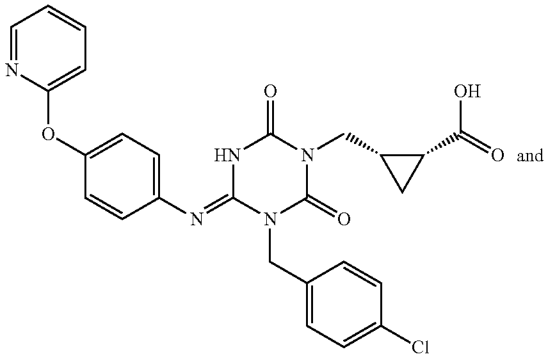

and

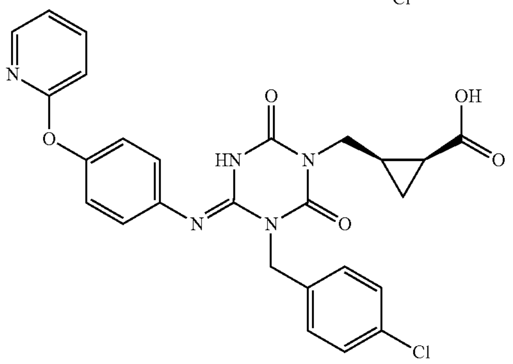

Step 1: Methyl (±) cis-2-(hydroxymethyl)cyclopropan-1-carboxylate (52 mg, 403.01 μmol), 1-(4-chlorobenzyl)-6-(ethylthio)-1,3,5-triazin-2,4(1H,3H)-dione (100 mg, 335.84 μmol, 1239691-22-5) and triphenylphosphine (132.13 mg, 503.76 μmol) were added to DCM (10 mL), to which diethyl azodicarboxylate (87.73 mg, 503.76 μmol, 79.04 μL) was added under argon protection. The reaction solution was stirred at room temperature for 1 hour. The reaction solution was spin-dried under reduced pressure. The residue was purified by silica gel column chromatography with eluent system (petroleum ether/ethyl acetate: 1/0 to 1/1) to give methyl (±) cis-methyl 2-((5-(4-chlorobenzyl)-4-(ethylthio)-2,6-dioxo-5, 6-dihydro-1,3,5-triazin-1(2H)-yl)methyl)cyclopropaneformate (125 mg). MS m/z (ESI): 410.1 $[M+H]^+$.

Step 2: Methyl (±) cis-methyl 2-((5-(4-chlorobenzyl)-4-(ethylthio)-2,6-dioxo-5, 6-dihydro-1,3,5-triazin-1(2H)-yl)methyl)cyclopropaneformate (50 μmg, 121.99 μmol) and 4-(2-pyridinoxy)aniline (22.71 mg, 121.99 μmol) were dissolved in pivalic acid (3 mL). The reaction system was stirred at 120° C. for 5 hours. Saturated sodium bicarbonate solution (30 mL) was added. The resultant was extracted with DCM (30 mL×3). The organic phase was dried, filtered, and concentrated under reduced pressure to give (±) cis-methyl 2-((-3-(4-chlorobenzyl)-2,6-dioxo-4-(4-(pyridin-2-yloxy)phenylimino)-1,3,5-triazin-1-yl)methyl)cyclopropanecarboxylic acid (65 mg). MS m/z (ESI): 534.2 $[M+H]^+$.

Step 3: (±) Cis-methyl 2-((-3-(4-chlorobenzyl)-2,6-dioxo-4-(4-(pyridin-2-yloxy)phenylimino)-1,3,5-triazin-1-yl)

methyl)cyclopropanecarboxylic acid (65 mg, 121.73 μmol) was added to a solvent mixture of THE (10 mL), methanol (2 mL) and water (2 mL), to which lithium hydroxide monohydrate (10.22 mg, 243.46 μmol) was then added. The reaction solution was stirred at room temperature for 4 hours. The reaction solution was neutralized with 1 N hydrochloric acid solution and concentrated under reduced pressure. The residue was purified by preparative liquid chromatography (preparative column: water-sunfire; system: A: water +0.045% formic acid, B: acetonitrile; wavelength: 254/214 nm; gradient: 5% to 30% acetonitrile) to give (±) cis-2-((3-(4-chlorobenzyl)-2,6-dioxo-4-(4-(pyridin-2-yloxy)phenylimino)-1,3,5-triazin-1-yl)methyl)cyclopropanecarboxylic acid H1 (16.21 mg). $^1$H NMR (400 MHz, DMSO-$d_6$) δ (ppm): 12.16 (s, 1H), 9.33 (s, 1H), 8.17-8.11 (m, 1H), 7.84 (t, J=7.0 Hz, 1H), 7.56-7.23 (m, 6H), 7.12-7.02 (m, 4H), 5.28 (s, 2H), 4.07-3.95 (m, 1H), 3.87-3.83 (m, 1H), 1.67-1.61 (m, 1H), 1.50-1.45 (m, 1H), 0.97 (t, J=6.8 Hz, 2H). MS m/z (ESI): 520.1 [M+H]$^+$.

Example 2: Preparation of (±) trans-2-((3-(4-chlorobenzyl)-2,6-dioxo-4-(4-(pyridin-2-yloxy)phenylimino)-1,3,5-triazin-1-yl)methyl)cyclopropanecarboxylic acid H2

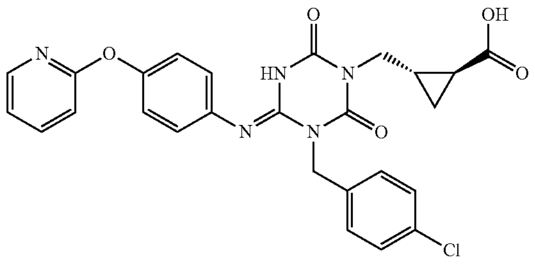

and

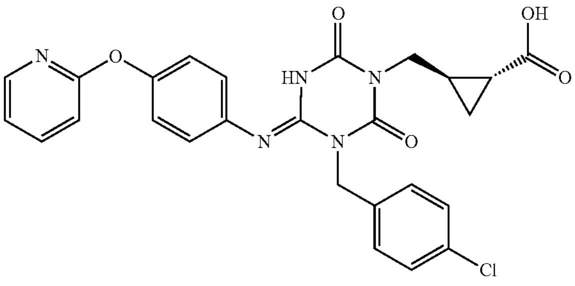

(±) Trans-2-((3-(4-chlorobenzyl)-2,6-dioxo-4-(4-(pyridin-2-yloxy)phenylimino)-1,3,5-triazin-1-yl)methyl)cyclopropanecarboxylic acid H2 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate. MS m/z (ESI): 520.2[M+1]$^+$; $^1$H NMR (400 MHz, DMSO-$d_6$) δ (ppm): 12.03 (s, 1H), 9.37 (s, 1H), 8.16-8.15 (m, 1H), 7.83-7.82 (m, 1H), 7.38-7.37 (m, 6H), 7.10-7.09 (m, 3H), 7.02-7.01 (m, 1H), 5.28 (s, 2H), 3.79-3.60 (m, 2H), 1.65-1.54 (m, 2H), 0.94-0.92 (m, 2H).

Example 3: Preparation of (±) trans-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid H3

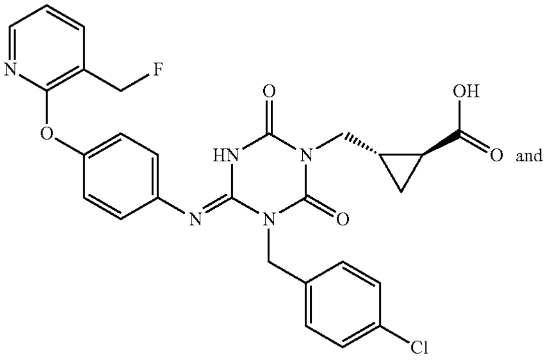

and

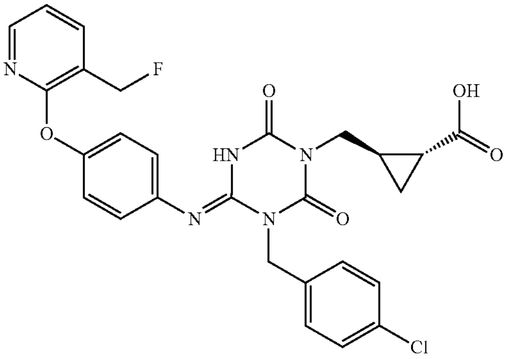

(±) Trans-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid H3 was prepared by referring to the preparation method of Example 1, and the difference is that the compound methyl (±) cis-2-(hydroxymethyl)cyclopropan-1-carboxylate was replaced with methyl trans-2-(hydroxymethyl)cyclopropan-1-carboxylate and 4-(2-pyridyloxy)aniline was replaced with intermediate V1. $^1$H NMR (400 MHz, DMSO-$d_6$) δ (ppm): 12.13 (s, 1H), 9.38 (s, 1H), 8.14 (d, J=4.7 Hz, 1H), 7.94 (d, J=7.3 Hz, 1H), 7.44-7.34 (m, 6H), 7.21-7.07 (m, 3H), 5.62 (s, 1H), 5.50 (s, 1H), 5.28 (s, 2H), 3.78-3.61 (m, 2H), 1.60-1.57 (m, 2H), 0.99-0.87 (m, 2H). MS m/z (ESI): 552.2 [M+H]$^+$.

Example 4: Preparation of (±) trans-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid H4

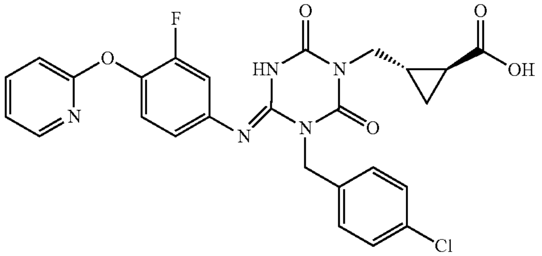

and

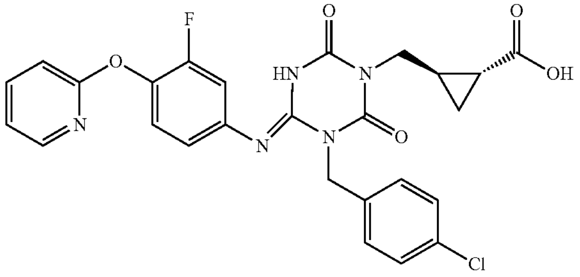

(±) Trans-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid H4 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate and 4-(2-pyridyloxy)aniline was replaced with intermediate V3. MS m/z (ESI): 538.2 $[M+H]^+$. $^1H$ NMR (400 MHz, DMSO-$d_6$) δ (ppm): 12.13 (s, 1H), 9.46 (s, 1H), 8.14-8.06 (m, 1H), 7.85 (td, J=11.9, 10.6, 5.6 Hz, 1H), 7.51-7.24 (m, 5H), 7.23-6.98 (m, 3H), 6.69 (dd, J=70.9, 10.3 Hz, 1H), 5.38-5.02 (m, 2H), 3.87-3.56 (m, 2H), 1.59 (t, J=6.9 Hz, 2H), 0.93 (q, J=7.1, 6.3 Hz, 2H).

Example 5: Preparation of (±) trans-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid H5

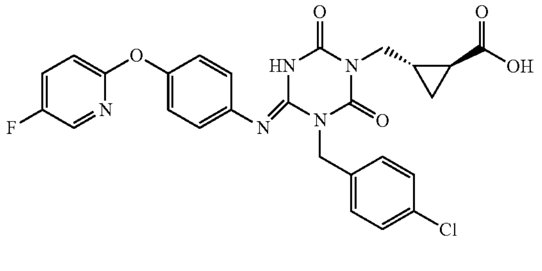

and

-continued

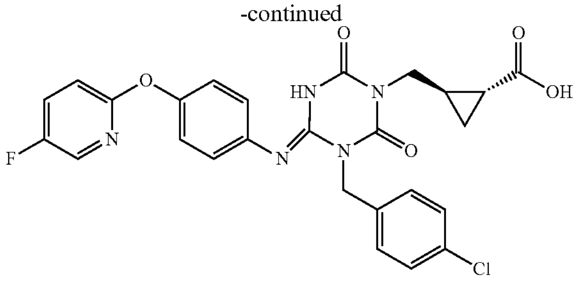

Step 1: Methyl (±) trans-2-((3-(4-chlorobenzyl)-4-ethylthio-2,6-dioxo-3,6-dihydro-1,3,5-triazin-1(2H)-yl)methyl) cyclopropan-1-carboxylate V6 (1.9 g, 4.64 mmol) and 4-((5-fluoropyridin-2-yl)oxy) aniline V4 (947 mg, 4.64 mmol) were dissolved in pivalic acid (10 mL). The reaction system was stirred at 120° C. for 3 hours. The reaction solution was neutralized with saturated sodium bicarbonate, extracted with dichloromethane, and dried with anhydrous sodium sulfate. The resultant was spin-dried under reduced pressure. The residue was purified by silica gel column chromatography (20 g, 0 to 5% MeOH/DCM) to give methyl (±) trans-2-((3-(4-chlorobenzyl)-4-((4-((5-fluoropyridin-2-yl)oxy)phenyl) amino)-2,6-dioxo-3,6-dihydro-1,3,5-triazin-1(2H)-yl)methyl) cyclopropan-1-carboxylate (2 g). MS m/z (ESI): 551.4 $[M+H]^+$.

Step 2: Methyl (±) trans-2-((3-(4-chlorobenzyl)-4-((4-((5-fluoropyridin-2-yl)oxy)phenyl) amino)-2,6-dioxo-3,6-dihydro-1,3,5-triazin-1 (2H)-yl)methyl) cyclopropan-1-carboxylate (2.00 g, 3.62 mmol) was dissolved in a solvent mixture of methanol (10 mL) and water (10 mL). LiOH (433.91 mg, 18.12 mmol) was then added. The reaction system was stirred at room temperature for 16 hours. The solvent was spin-dried. The residue was purified by preparative liquid chromatography (preparative column: 21.2×250 mm C18 column; system: 10 mM HCOOH $H_2O$; wavelength: 254/214 nm; gradient: 30% to 60% acetonitrile) to give (±) trans-2-((3-(4-chlorobenzyl)-4-((4-((5-fluoropyridin-2-yl)oxy)phenyl) imino)-2,6-dioxo-1,3,5-triazin-1-yl) methyl) cyclopropan-1-carboxylic acid H5 (1.2 g). MS m/z (ESI): 538.1 [M+1]. $^1$HNMR (400 MHz, DMSO-$d_6$) δ (ppm): 8.14 (d, J=3.1 Hz, 1H), 7.84-7.76 (m, 1H), 7.38 (dd, J=19.6, 8.5 Hz, 4H), 7.29-7.00 (m, 5H), 5.23 (s, 2H), 3.67 (ddd, J=20.7, 13.7, 6.5 Hz, 2H), 1.57 (d, J=3.8 Hz, 2H), 0.97-0.88 (m, 2H).

Example 5-1: Preparation of enantiomers H5-P1 and H5-P2 of (±) trans-2-((3-(4-chlorobenzyl)-4-((4-((5-fluoropyridin-2-yl)oxy)phenyl)imino)-2,6-dioxo-1,3,5-triazin-1-yl)methyl) cyclopropan-1-carboxylic acid (±) trans-2-((3-(4-chlorobenzyl)-4-((4-((5-fluoropyridin-2-yl)oxy)phenyl)imino)-2,6-dioxo-1,3,5-triazin-1-yl) methyl) cyclopropan-1-carboxylic acid was separated through a chiral HPLC column (system: Waters UPCC; column: IG 4.6×100 mm 5 um solvent: methanol; flow rate: 3.0 mL/min) to give enantiomers H5-P1 (retention time: 1.960 min) and H5-P2 (retention time: 2.678 min), respectively.

Example 5-2: (1S,2S)-2-((3-(4-chlorobenzyl)-4-((4-((5-fluoropyridin-2-yl)oxy)phenyl)imino)-2,6-dioxo-1,3,5-triazin-1-yl)methyl) cyclopropan-1-carboxylic acid

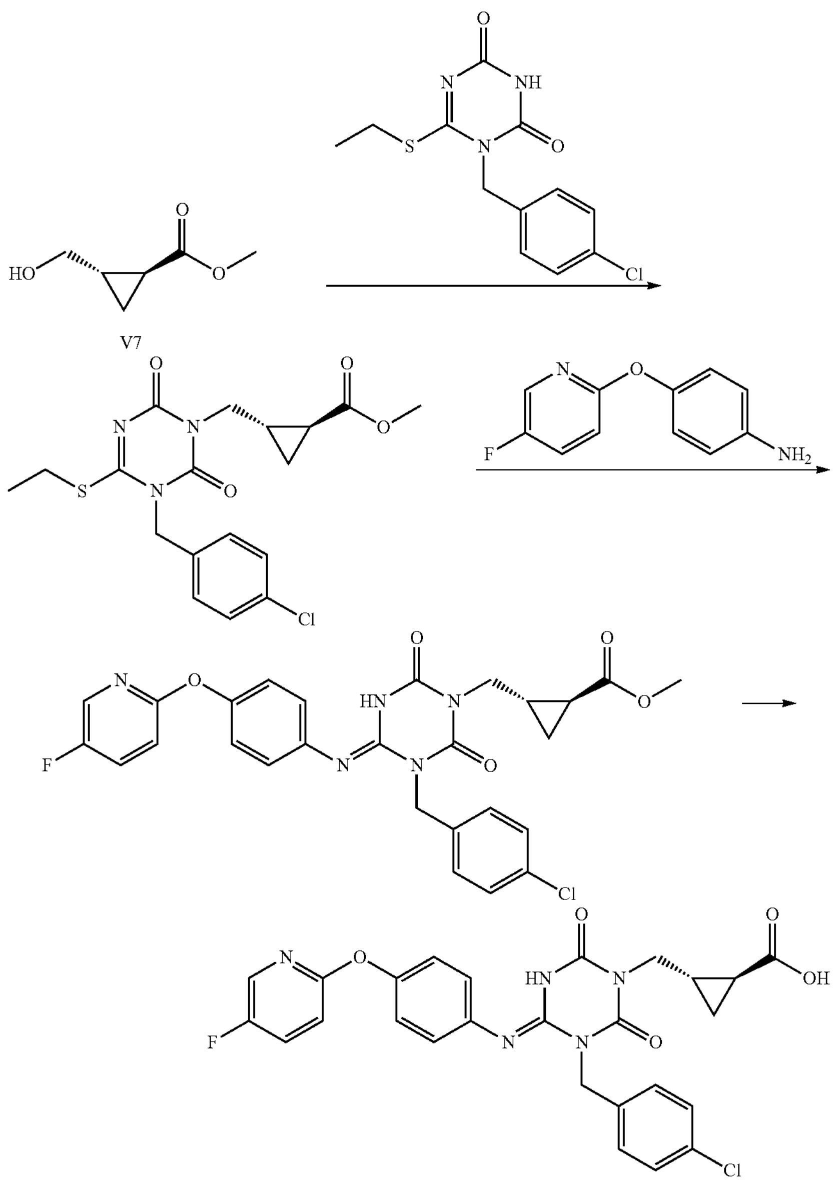

Step 1: Methyl (1S,2S)-2-(hydroxymethyl)cyclopropan-1-carboxylate V7 (39 g, 0.3 mol), 1-(4--chlorobenzyl)-6-(ethylthio)-1,3,5-triazin-2,4(1H,3H)-dione (89 g, 0.3 mol) and triphenylphosphine (102 g, 0.39 mol) were suspended in dry tetrahydrofuran (10 mL), to which DEAD (68 g, 0.39 mol) was added dropwise. The reaction solution was gradually clarified and was stirred at room temperature overnight. The reaction solution was concentrated. The residue was purified by silica gel column chromatography (ethyl acetate/petroleum ether: 1/2) to give methyl (1S,2S)-2-((3-(4-chlorobenzyl)-4-ethylthio-2,6-dioxo-3,6-dihydro-1,3,5-triazin-1(2H)-yl)methyl)cyclopropan-1-carboxylate (135 g). MS m/z (ESI): 410.1 $[M+1]^+$.

Step 2: Methyl (1S,2S)-2-((3-(4-chlorobenzyl)-4-ethylthio-2,6-dioxo-3,6-dihydro-1,3,5-triazin-1(2H)-yl)methyl) cyclopropan-1-carboxylate (120 g, 0.293 mol) and 4-((5-fluoropyridin-2-yl)oxy)aniline V4 (60 g, 0.293 mol) were added to a round bottomed flask, and the mixture was then added to pivalic acid (400 g). The reaction solution was then heated up to 130° C. and stirred for 5 hours. The reaction solution was cooled down and diluted with water (800 mL). The resultant was adjusted with sodium carbonate to pH=7-8 and extracted with dichloromethane. The combined organic phase was dried, filtered, and concentrated. The residue was purified by column chromatography (ethyl acetate/petroleum ether: 1/3) to give methyl (1S,2S)-2-((3-(4-chlorobenzyl)-4-((4-((5-fluoropyridin-2-yl)oxy)phenyl)amino)-2,6- dioxo-1,3,5-triazin-1-yl)methyl)cyclopropan-1-carboxylate (150 g). MS m/z (ESI): 552.1 $[M+1]^+$.

Step 3: Methyl (1S,2S)-2-((3-(4-chlorobenzyl)-4-((4-((5-fluoropyridin-2-yl)oxy)phenyl)amino)-2,6-dioxo-1,3,5-triazin-1-yl)methyl)cyclopropan-1-carboxylate (150 g, 0.272 mol) was dissolved in a solvent mixture of tetrahydrofuran/methanol/water (300 mL/100 mL/100 mL), to which lithium hydroxide (monohydrate) (22 g, 0.544 mol) was added. The reaction solution was stirred at room temperature overnight, filtered, and concentrated. The residue was diluted with water, and extracted twice with ethyl acetate. The aqueous phase was adjusted with a 3 M hydrochloric acid solution to pH of around 5 to 6, then was extracted with ethyl acetate. The organic phases obtained by the second extraction were combined and the resultant was washed with saturated sodium chloride solution, dried with anhydrous sodium sulfate, concentrated, and purified (ethyl acetate/petroleum ether=1/3) to give (1S,2S)-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid (100 g). MS m/z (ESI): 538.1 $[M+1]^+$. $^1$H NMR (400 MHz, DMSO-$d_6$) δ (ppm): 8.15 (d, J=3.1 Hz, 1H), 7.82-7.81 (m, 1H), 7.48-7.30 (m, 6H), 7.12-7.10 (m, 3H), 5.36-5.19 (m, 2H), 3.67-3.64 (m, 2H), 1.63-1.54 (m, 2H), 1.00-0.87 (m, 2H).

The (1S,2S)-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid synthesized above was compared with the enantiomer P1 and enantiomer P2 in Example 5-1 through a chiral HPLC column (system: Waters UPCC; column: IG 4.6*100 mm 5 m; solvent: methanol; flow rate: 3.0 mL/min). The retention time of enantiomer P1 is consistent with that of (1S,2S)-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid. Therefore, it is inferred that the absolute configuration of enantiomer P1 is (1S,2S) configuration, i.e., H5-P1 is (1S,2S)-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid. Therefore, the absolute configuration of enantiomer P2 is (1R,2R) configuration, i.e., H5-P2 is (1R,2R)-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid.

Example 6: Preparation of (±) trans-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid H6

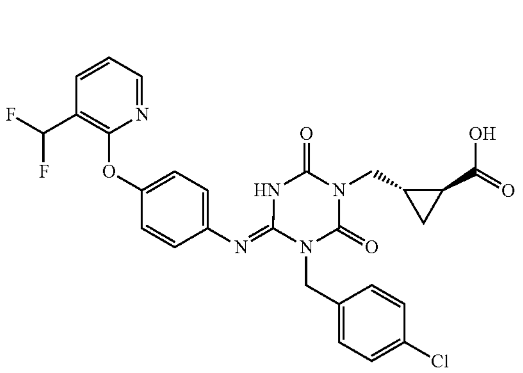

and

-continued

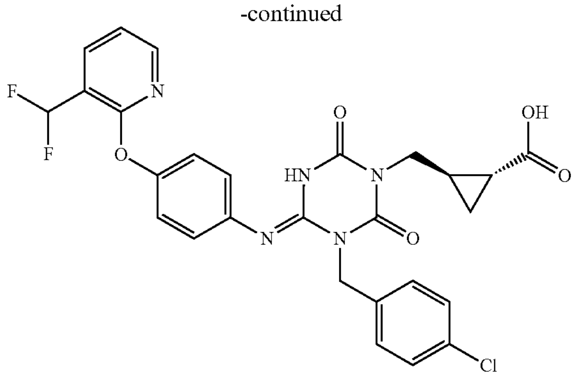

(±) Trans-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid H6 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate and 4-(2-pyridyloxy)aniline was replaced with intermediate V2. $^1$H NMR (400 MHz, DMSO-$d_6$) δ (ppm): 12.12 (s, 1H), 9.40 (s, 1H), 8.27 (d, J=4.2 Hz, 1H), 8.08 (d, J=7.3 Hz, 1H), 7.52-6.95 (m, 10H), 5.25 (s, 2H), 3.79-3.57 (m, 2H), 1.59-1.56 (m, 2H), 0.98-0.87 (m, 2H). MS m/z (ESI): 570.2 $[M+H]^+$.

Example 7: Preparation of (±) trans-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid H7

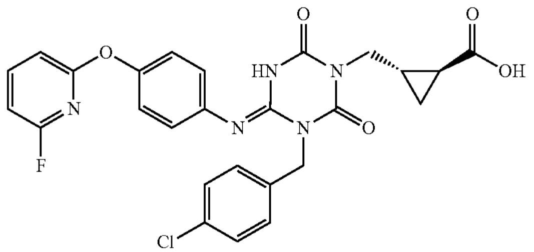

and

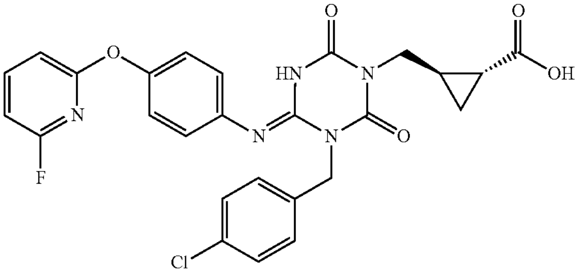

(±) Trans-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid H7 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate and 4-(2-pyridyloxy)aniline was replaced with 4-[(6-fluoro-2-pyridinyl)oxy]-aniline (CAS. NO: 62566-16-9).

MS m/z (ESI): 538.1 $[M+1]^+$. H NMR (400 MHz, DMSO-$d_6$) δ (ppm): 12.11 (s, 1H), 9.39 (s, 1H), 8.01-7.97 (m, 1H), 7.41-7.37 (m, 6H), 7.16-7.13 (m, 2H), 6.91-6.85 (m, 2H), 5.28 (s, 2H), 3.73-3.62 (m, 2H), 1.60-1.57 (m, 2H), 0.97-0.90 (m, 2H).

Example 8: Preparation of (±) trans-2-((3-(4-chlorobenzyl)-4-((4-((3-fluoropyridin-2-yl)oxy)phenyl)imino)-2,6-dioxo-1,3,5-triazin-1-yl)methyl)cyclopropane-1-carboxylic acid H8

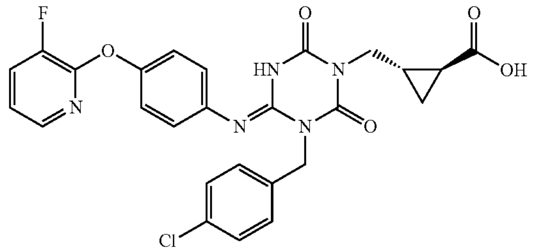

and

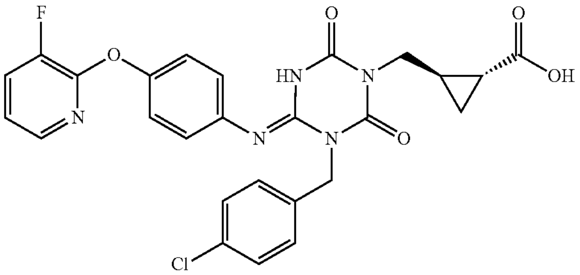

(±) Trans-2-((3-(4-chlorobenzyl)-4-((4-((3-fluoropyridin-2-yl)oxy)phenyl)imino)-2,6-dioxo-1,3,5-triazin-1-yl)methyl)cyclopropane-1-carboxylic acid H8 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate and 4-(2-pyridyloxy)aniline was replaced with 4-[(3-fluoro-2-pyridinyl)oxy]-aniline (CAS. NO: 1342511-06-1). MS m/z (ESI): 538.1 $[M+1]^+$. $^{1}$H NMR (400 MHz, DMSO-$d_6$) δ (ppm): 12.10 (s, 1H), 9.39 (s, 1H), 7.95-7.82 (m, 2H), 7.44-7.36 (m, 6H), 7.20-7.15 (m, 3H), 5.28 (s, 2H), 3.75-3.62 (m, 2H), 1.60-1.57 (m, 2H), 0.95-0.83 (m, 2H).

Example 9: Preparation of (±) trans-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid H9

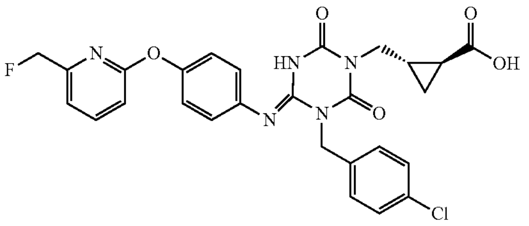

and

-continued

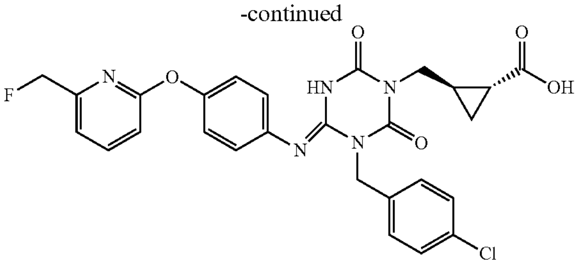

(±) Trans-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid H9 was prepared by referring to the preparation method of Example 1, and the difference is that the compound methyl (±) cis-2-(hydroxymethyl)cyclopropan-1-carboxylate was replaced with methyl (±) trans-2-(hydroxymethyl)cyclopropan-1-carboxylate and 4-(2-pyridyloxy)aniline was replaced with intermediate V5. MS m/z (ESI): 552.1 $[M+1]^+$. $^{1}$H NMR (400 MHz, DMSO-$d_6$) δ (ppm): 12.14 (s, 1H), 9.37 (s, 1H), 7.91 (m, 1H), 7.49-7.28 (m, 6H), 7.20 (d, J=7.4 Hz, 1H), 7.12-7.11 (m, 2H), 6.99 (d, J=6.5 Hz, 1H), 5.35 (s, 1H), 5.25-5.24 (m, 2H), 3.64-3.63 (m, 3H), 1.58-1.57(m, 2H), 0.99-0.87 (in, 2H).

Test Example 1: Screening Compounds for Antagonistic Activity Against hP2X3/hP2X2/3 Receptors by FLIPR Assay Materials:

| Name | Supplier | Article number |
|---|---|---|
| FLIPR ® Calcium 4 Assay Kit | Molecular Devices | R8141 |
| FBS | Gibco | 10099-141 |
| DMEM | Gibco | 11965 |
| Hygromycin B | Invitrogen | 10687010 |
| G418 disulfate salt | SIGMA | G5013 |
| 384-well test plate | Corning | CC3712 |
| 384-well compound plate | Corning | CC3657 |
| 384-well polypropylene microporous plate conforming to Echo standard | LABCYTE | P-05525 |
| Probenecid | Sigma | P8761-25G |
| 1x HBSS | Invitrogen | 14025 |
| ATP hydrolase | Sigma | A7646 |
| HEPES | Invitrogen | 15630-080 |
| Versene | Gibco | 15040066 |

Cell preparation: Cells 1321N1/hP2X3 and cells 1321N1/hP2X2/3 (supplier: Chempartner) were stable transfected with Versene digestive solution. After centrifugation, the cells were suspended using plate medium (DMEM+100% DFBS) and counted. The cells were adjusted to $3\times10^5$ cells/mL. Each of the 384-well test plates was covered with 50 μL cells and cultured in a 500 $CO_2$ incubator at 37° C. for 16 hours to 24 hours.

Cell Culture Medium Formula:

| | Working solution concentration | Stock solution concentration | Dilution factor | Required volume (mL) |
|---|---|---|---|---|
| hP2X3 | | | | |
| DMEM | 1* | 1* | 1 | 447.006 |
| FBS | 10% | 100% | 10 | 50 |

-continued

| | Working solution concentration | Stock solution concentration | Dilution factor | Required volume (mL) |
|---|---|---|---|---|
| G418 disulfate salt | 300 μg/ml | 50 mg/ml | 167 | 2.994012 |
| | | | Sample size | 500 |
| hP2X2/3 | | | | |
| DMEM | 1* | 1* | 1 | 447.7489 |
| FBS | 10% | 100% | 10 | 50 |
| G418 disulfate salt | 150 μg/mL | 50 mg/mL | 333 | 1.501502 |
| Hygromycin B | 75 μg/mL | 50 mg/mL | 667 | 0.749625 |
| | | | Sample size | 500 |

Experimental Dye Formula:

| hP2X3 | Working solution concentration | Stock solution concentration | Dilution factor | Required volume (mL) |
|---|---|---|---|---|
| 10* dye stock | 0.5* | 10* | 20 | 0.7 |
| Probenecid | 1.25 | 0.25 | 200 | 0.07 |
| Test buffer | 1* | 1* | 1 | 13.23 |
| ATP hydrolase | 0.5 U/mL | 10 μL = 1 U | 200 | 0.07 |
| | | | Sample size | 14 |

| hP2X2/3 | Working solution concentration | Stock solution concentration | Stock solution concentration | Required volume (mL) |
|---|---|---|---|---|
| 10* dye stock | 0.5* | 10* | 20 | 0.7 |
| Probenecid | 1.25 | 0.25 | 200 | 0.07 |
| Test buffer | 1* | 1* | 1 | 13.23 |
| | | | Sample size | 14 |

Compound preparation: 1. Test sample: test compound at a concentration 180 times the required concentration (54 mM DMSO stock solution) was prepared using DMSO in a 384-well polypropylene microporous plate conforming to Echo standard, 500 nL of which was added to each well of a 384-well compound plate. Then 30 μL of test buffer (1*HIBSS+2 mM $CaCl_2$+20 mM HEPES containing 1.26 mM $Ca^{2+}$) was added to each well. The 384-well compound plate was shook for 20 min to 40 min to mix well.

2. Agonist: agonist (α,μ-meATP) at a concentration 3 times the required concentration (the final concentration of 3000 nM is required for both $hP2X_3$ and $hP2X_{2/3}$ cells) was prepared with the test buffer. 45 μL of agonist was added to each well of the 384-well compound plate.

Dye incubation: The cell plate was taken out. The supernatant was removed. 30 uL of Dye (FLTPR® Calcium 4 Assay Kit, test buffer diluted) was added to each well. The cells were incubated for 1 hour.

FLTPR detection: 15 μL of compound was added to each well of the cell plate (FLTPR instrument sampling). After 15 minutes, 22.5 μL of agonist was added to each well. Fluorescence signals (excitation wavelength of 470 nm to 495 nm, emission wavelength of 515 nm to 575 nm) were detected.

Data processing: the difference between the peak value and the valley value of the signal was taken as the basic data. The highest concentration of positive drug was taken as 100% inhibition rate, and DMSO data was taken as 0% inhibition rate. The inhibition curves of compounds were fitted by log (inhibitor) vs. response—Variable slope on Graphpad prism 6 and the $IC_{50}$ value was calculated.

Experimental homogeneity standard: each plate was subjected to ≥12 max values (DMSO action results) and ≥12 min values (highest concentration positive drug action results), and the Z value was calculated. If Z≥0.5, it is considered that the parallel wells are homogenous and the data is reliable. The calculation formula for Z value is as follows: Z=1−3*(SDmax+SDmin)/(MEANmax MEANmin). The test results are shown in Tables 4 and 5.

TABLE 4

P2X3 Inhibitory Activity of the Compounds

| Compound number | P2X3 ($IC_{50}$/nM) |
|---|---|
| H5-P1 | 23 |
| H5-P2 | 106 |
| H7 | 73 |
| H8 | 148 |

TABLE 5

Multiple of P2X2/3 inhibitory activity and P2X3 inhibitory activity of the compounds

| Compound number | Selectivity multiple |
|---|---|
| H1 | 27 |
| H2 | 151 |
| H5 | 251 |
| H5-P1 | 590 |
| H5-P2 | 176 |
| H7 | 114 |
| H8 | 238 |

It can be seen from Table 4 and Table 5 that the example compounds of the application have high P2X3 inhibitory activity and low P2X2/3 inhibitory activity, and have high inhibitory selectivity. Further, the comparison between H1 and H2 shows the compound with the form of trans-structure of

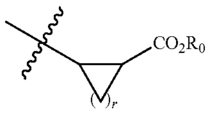

has higher P2X3 selective inhibitory activity than the compound with the form of cis-structure. The comparison between H5-P1 and H5-P2 shows that the compound with

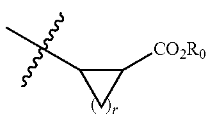

as

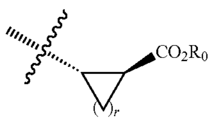

as configuration has higher P2X3 selective inhibition activity than the compound with

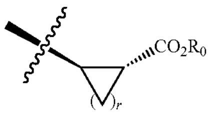

configuration.

Test Example 2: Evaluation of Analgesic Effect of Rat CFA Inflammatory Pain Model Experimental animals: 50 male SD rats with a weight of 230 g to 260 g were used. All the experimental animals were purchased from Beijing Weitonglihua Experimental Animal Technology Co., LTD. After purchase, food and water were supplied in the way of free feeding. The feeding temperature was 20° C. to 25° C. The humidity was 40% to 70%. The animals were kept in separate cages and labeled using the tail labeling method. Experimental design grouping and medicament treatment are shown in Table 6.

TABLE 6

Experimental design grouping and medicament treatment

| Group | Medicament for treatment | Dosage (mg/kg) | Dosing volume (mL/kg) | Route of administration | Number of animals |
|---|---|---|---|---|---|
| 1 | Solvent group | — | 10 | Once a day, orally | 10 |
| 2 | Naproxen | 100 | 10 | Once a day, orally | 10 |
| 3 | H5-P1 | 30 | 10 | Once a day, orally | 10 |
| 4 | H5-P1 | 60 | 10 | Once a day, orally | 10 |
| 5 | Untreated group | — | — | — | 10 |

Figure 2:
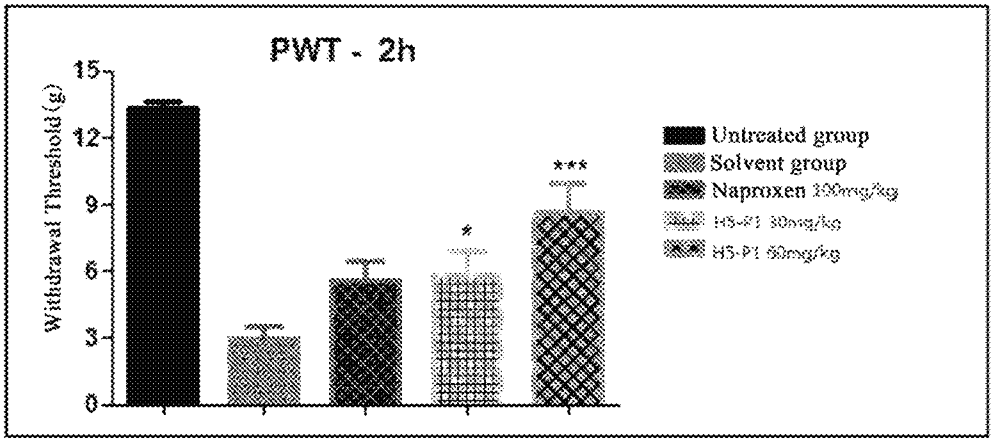
FIG. 2 shows results of paw withdrawal threshold in different treatment groups at 2 hours after administration.
Figure 3:
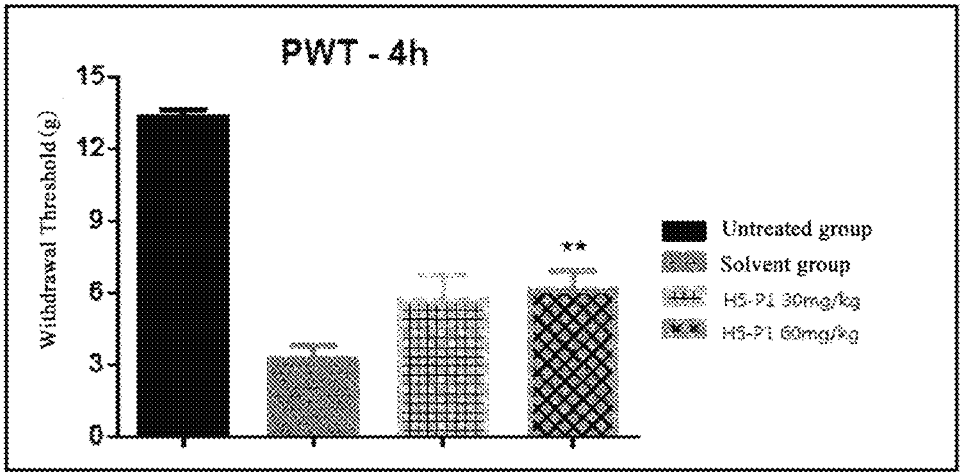
FIG. 3 shows the results of paw withdrawal threshold in different treatment groups at 4 hours after administration.

An emulsion was obtained by mixing full Freund's adjuvant with saline in equal amount. A certain amount of the emulsion was injected subcutaneously into the rats. The animal was placed in a specially designed multi-unit metal mesh cage for pain detection and allowed to acclimate for 15 minutes. After the animal's grooming and investigation activities were completed and acclimated to the detection environment, a series of calibrated von Frey filaments (0.4, 0.6, 1.0, 1.4, 2, 4, 6, 8, 10, 15) were continuously applied to the back paw until a withdrawal reflex reaction occurred. The tester conducted blind test on the experiment, and the experimental results were expressed as "mean±standard deviation". The data of each group are analyzed by GraphPad Prism 5 t test, with statistical difference at $P<0.05$. The specific experimental results are shown in FIG. 2 and FIG. 3. It can be seen from FIG. 2 and FIG. 3 that compound H5-P1 significantly inhibits mechanical pain hypersensitivity in the rat CFA inflammatory pain model, the effective dose in the rat CFA inflammatory pain model is 30 mg/kg, and the medium-high dose (60 mg/kg) still has a good analgesic effect 4 hours after administration.

Test Example 3: Toxicity Test

Experimental Animals:

There were 16 male and 16 female SD rats with SPF grade. Male SD rats weighed about 240 g and were 6 to 9 weeks old. Female SD rats weighed about 200 g and were 6 to 9 weeks old. All the experimental animals were purchased from Zhejiang Weitonglihua Experimental Animal Technology Co., LTD. After purchase, food and water were supplied in the way of free feeding. The feeding temperature was 20° C. to 26° C. The humidity was 40% to 70%. The number of air changes per hour was ≥15 times, and 100% fresh air was used. Automatic lighting and alternating light and dark every 12 hours were used. Male and female are kept in separate cages, with no more than 5 rats per cage.

Animals in each group were randomly divided according to gender and body weight, and were given the medicament once a day for 14 days according to the dose design in Table 7. Toxicokinetic blood sampling was performed in each dose group 30 min, 1 hr, 4 hr, 7 hr, 10 hr and 24 hr before and after the first and last administration, respectively, to investigate the toxicokinetic process in SD rats of each group. The results are as shown in Table 8.

TABLE 7

Experimental dose design

| Group order | Group | Dosage (mg/kg) | Dosage concen-tration (mg/mL) | Main test group (F/M) | TK group * (F/M) |
|---|---|---|---|---|---|
| 1 | Solvent control group (5% Solutol + 1% RC591 aqueous solution) | 0 | 0 | 4/4 | — |
| 2 | H5-P1 | 100 | 10 | 4/4 | 3/3 |
| 3 | D1 | 100 | 10 | 2/2 | 3/3 |

Calculation Basis for Safety Windows:

The effective dose of compound H5-P1 in the rat pain model is 30 mg/kg, at which Cmax is about 18.4 µg/mL and AUC is about 249 hr*µg/mL. The effective dose of compound D1 in the rat pain pharmacological model is 60 mg/kg, at which Cmax is about 141 µg/mL and AUC is about 1566 hr*µg/mL.

TABLE 8

Toxicokinetic analysis of rat toxicity studies

| | | | $C_{max}$(ug/mL) | | $AUC_{0t}$ (hr*µg/mL) | | Safety window | |
|---|---|---|---|---|---|---|---|---|
| Sample | Gender | Dosage (mg/kg) | First administration | Last administration | First administration | Last administration | $AUC_{0t}$ | $C_{max}$ |
| H5-P1 | Female | 100 | 112 | 135 | 1424 | 1745 | 7.0 | 7.3 |
| | Male | 100 | 101 | 162 | 1462 | 2387 | 9.6 | 8.8 |
| D1 | Female | 100 | 185 | 156 | 2415 | 2149 | 1.4 | 1.1 |
| | Male | 100 | 200 | 188 | 2767 | 2536 | 1.6 | 1.3 |

During the experiment, there was no significant abnormality in the weight of animals of each group, and no animals were found to be dead or nearly dead. From the data in Table 8, it can also be seen that compound H5-P1 has a high safety window.

The structure of positive compound D1 in test example 3 is as follows:

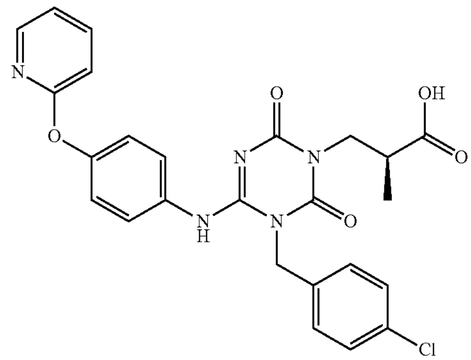 [SMILES: C[C@@H](Cn1c(=O)nc(Nc2ccc(Oc3ccccn3)cc2)n(Cc2ccc(Cl)cc2)c1=O)C(=O)O]

All documents mentioned in the present application are cited as references in the present application as if each document were cited individually as a reference. It is further to be understood that after reading the foregoing teachings of the present application, those skilled in the art may make various alterations or modifications to the present application, and these equivalent forms will likewise fall within the scope of the claims appended to this application.

The invention claimed is:

1. A compound of formula (I), or a pharmaceutically acceptable salt thereof, or a stereoisomer thereof:

(I)

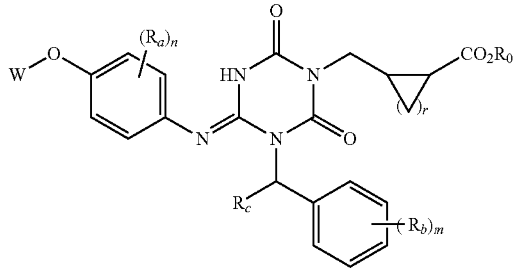

wherein, r is 1, 2, or 3;

W is a benzene ring or a 5- to 6-membered heteroaryl ring; the benzene ring and the 5- to 6-membered heteroaryl ring are unsubstituted or substituted by 1, 2, 3, or 4 substituents each independently selected from the following group consisting of: deuterium, halogen, cyano, hydroxyl, carboxyl, $C_{1-8}$ alkyl, $C_{1-8}$ alkoxy, $C_{2-4}$ alkenyl, $C_{2-4}$ alkynyl, halo-$C_{1-8}$ alkyl, cyano-substituted $C_{1-8}$ alkyl, halo-$C_{1-8}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)C_{1-8}$ alkyl, —$C(O)OC_{1-8}$ alkyl, —$OC(O)C_{1-8}$ alkyl, $C_{3-6}$ cycloalkyl, $C_{3-6}$ cycloalkyloxy, 3- to 6-membered heterocycloalkyl, phenyl, and 5- to 6-membered heteroaryl; wherein, among the substituents, the 3- to 6-membered heterocycloalkyl, phenyl, and 5- to 6-membered heteroaryl are unsubstituted or substituted by 1, 2, or 3 substituents each independently selected from the following group consisting of: halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkyloxy, 3- to 6-membered heterocycloalkyl, phenyl, and 5- to 6-membered heteroaryl;

$(R_a)_n$ represents that hydrogen(s) on benzene ring is/are substituted with n $R_a$, and n is 0, 1, or 2; each $R_a$ is identical or different, and each $R_a$ is independently cyano, hydroxyl, carboxyl, halogen, $C_{1-8}$ alkyl, halo-$C_{1-8}$ alkyl, cyano-substituted $C_{1-8}$ alkyl, $C_{1-8}$ alkoxy, —$C(O)C_{1-8}$ alkyl, —$C(O)OC_{1-8}$ alkyl, —$OC(O)C_{1-8}$ alkyl, or —$C(O)NR_{a1}R_{b1}$;

$R_c$ is hydrogen, $C_{1-8}$ alkyl, $C_{3-8}$ cycloalkyl, $C_{1-8}$ alkoxy, cyano, hydroxyl, carboxyl, or halogen;

$(R_b)_m$ represents that hydrogen(s) on benzene ring is/are substituted with m $R_b$, and m is 0, 1, or 2; each $R_b$ is identical or different, and each $R_b$ is independently cyano, hydroxyl, carboxyl, halogen, $C_{1-8}$ alkyl, halo-$C_{1-8}$ alkyl, cyano-substituted $C_{1-8}$ alkyl, $C_{1-8}$ alkoxy, —$C(O)$ $C_{1-8}$ alkyl, —$C(O)OC_{1-8}$ alkyl, —$OC(O)C_{1-8}$ alkyl, or —$C(O)NR_{a1}R_{b1}$;

$R_0$ is hydrogen or $C_{1-6}$ alkyl;

$R_{a1}$ and $R_{b1}$ are each independently hydrogen or $C_{1-3}$ alkyl; or $R_{a1}$, $R_{b1}$ and nitrogen atom linked to Ral and Rbi together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —$S(O)C_{1-3}$ alkyl, —$C(O)NH_2$, —$C(O)NH(C_{1-3}$ alkyl), —$C(O)N(C_{1-3}$ alkyl$)_2$, —$C(O)OC_{1-3}$ alkyl, —$OC(O)C_{1-3}$ alkyl, $C_{3-6}$ cycloalkyl, $C_{3-6}$ cycloalkyloxy, and 3- to 6-membered heterocycloalkyl; and $R_{a0}$ and $R_{b0}$ are each independently hydrogen, $C_{1-3}$ alkyl, or acetyl; or $R_{a0}$, $R_{b0}$ and nitrogen atom linked to $R_{a0}$ and $R_{b0}$ together form a 4- to 6-membered saturated heteromonocycle; the 4- to 6-membered saturated heteromonocycle is unsubstituted or substituted by 1, 2, or 3 substituents each independently selected from the following group consisting of: deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, —$SO_2C_{1-3}$ alkyl, —$S(O)C_{1-3}$ alkyl, —$C(O)NH_2$, —$C(O)NH(C_{1-3}$ alkyl), —$C(O)N(C_{1-3}$ alkyl$)_2$, —$C(O)OC_{1-3}$ alkyl, —$OC(O)C_{1-3}$ alkyl, $C_{3-6}$ cycloalkyl, $C_{3-6}$ cycloalkyloxy, and 3-to-6-membered heterocycloalkyl.

2. The compound, or the pharmaceutically acceptable salt thereof, or the stereoisomer thereof according to claim 1, wherein r is 1.

3. The compound, or the pharmaceutically acceptable salt thereof, or the stereoisomer thereof according to claim 1, wherein W is

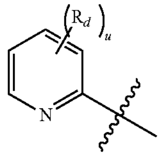

;

$(R_d)_u$ represents that hydrogen(s) on pyridine ring is/are substituted with u $R_d$, and u is 0, 1, or 2; each $R_a$ is identical or different, and each $R_d$ is independently deuterium, halogen, cyano, hydroxyl, carboxyl, $C_{1-8}$ alkyl, $C_{1-8}$ alkoxy, $C_{2-4}$ alkenyl, $C_{2-4}$ alkynyl, halo-$C_{1-8}$ alkyl, halo-$C_{1-8}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)C_{1-8}$ alkyl, —$C(O)OC_{1-8}$ alkyl, —$OC(O)C_{1-8}$ alkyl, $C_{3-6}$ cycloalkyl, $C_{3-6}$ cycloalkyloxy, 3- to 6-membered heterocycloalkyl, phenyl, or 5- to 6-membered heteroaryl; wherein the 3- to 6-membered heterocycloalkyl, phenyl, and 5 to 6-membered heteroaryl are unsubstituted or substituted by 1, 2, or 3 substituents each independently selected from the following group consisting of: halogen, cyano, hydroxyl, carboxyl, $C_{1-3}$ alkyl, $C_{1-3}$ alkoxy, $C_{2-4}$ alkenyl, $C_{2-4}$ alkynyl, halo-$C_{1-3}$ alkyl, halo-$C_{1-3}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkyloxy, 3- to 6-membered heterocycloalkyl, phenyl, and 5- to 6-membered heteroaryl.

4. The compound, or the pharmaceutically acceptable salt thereof, or the stereoisomer thereof according to claim 3, wherein u is 0 or 1; and $R_d$ is fluorine, chlorine, cyano, hydroxyl, carboxyl, $C_{1-3}$ alkyl, $C_{1-3}$ alkoxy, halo-$C_{1-3}$ alkyl, halo-$C_{1-3}$ alkoxy, $NR_{a0}R_{b0}$, —$SO_2C_{1-3}$ alkyl, —$S(O)C_{1-3}$ alkyl, —$C(O)NR_{a1}R_{b1}$, —$C(O)$ $C_{1-3}$ alkyl, —$C(O)OC_{1-3}$ alkyl, or —$OC(O)C_{1-3}$ alkyl.

5. The compound, or the pharmaceutically acceptable salt thereof, or the stereoisomer thereof according to claim 1, wherein W is

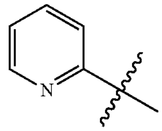,
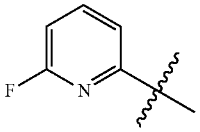,
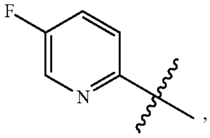,
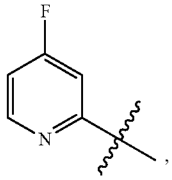,
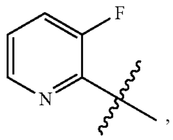,
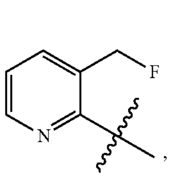,
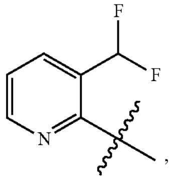,
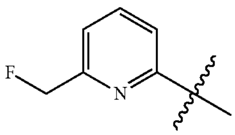 or
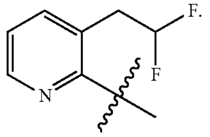.

6. The compound, or the pharmaceutically acceptable salt thereof, or the stereoisomer thereof according to claim 1, wherein

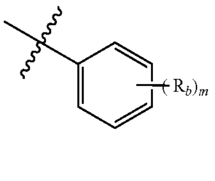

is

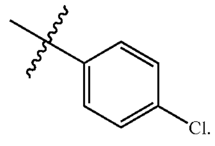 [SMILES: *c1ccc(Cl)cc1]

7. The compound, or the pharmaceutically acceptable salt thereof, or the stereoisomer thereof according to claim 1, wherein

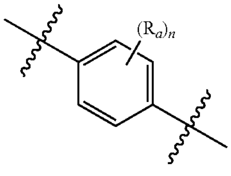

is

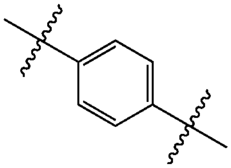 or 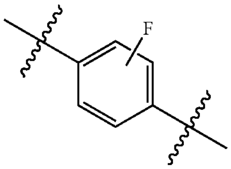.

8. The compound, or the pharmaceutically acceptable salt thereof, or the stereoisomer thereof according to claim 1, wherein n is 0.

9. The compound, or the pharmaceutically acceptable salt thereof, or the stereoisomer thereof according to claim 1, wherein $R_c$ is hydrogen.

10. The compound, or the pharmaceutically acceptable salt thereof, or the stereoisomer thereof according to claim 1, wherein $R_0$ is hydrogen.

11. The compound, or the pharmaceutically acceptable salt thereof, or the stereoisomer thereof according to claim 1, wherein

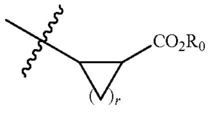

in the structure of formula (I) is in a form of a cis-structure or a trans-structure.

12. The compound, or the pharmaceutically acceptable salt thereof, or the stereoisomer thereof according to claim 3, wherein the compound of formula (I) is of the structure shown in formula (II):

(II)

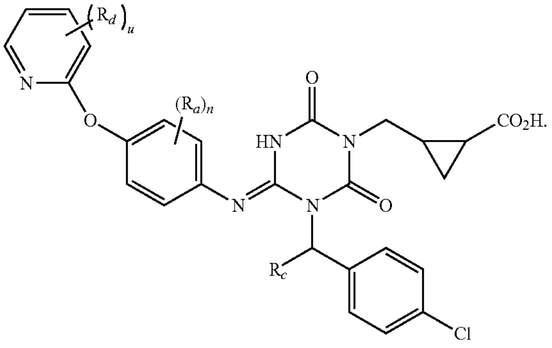

13. The compound, or the pharmaceutically acceptable salt thereof, or the stereoisomer thereof according to claim 3, wherein the compound of formula (I) is of the structure shown in formula (II-1):

(II-1)

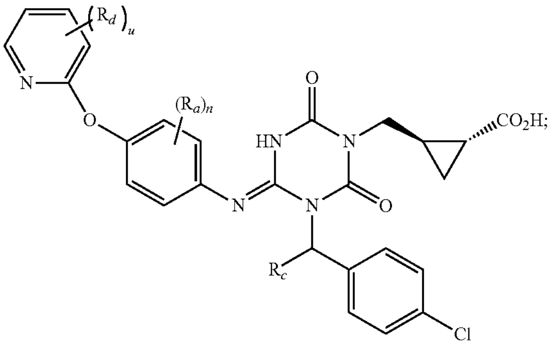

or the compound of formula (I) is of the structure shown in formula (II-2);

(II-2)

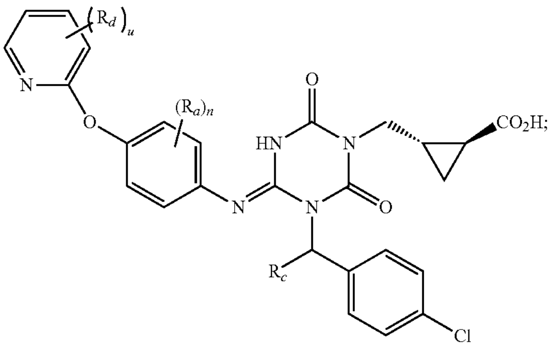

or the compound of formula (I) is of the structure shown in formula (II-3):

(II-3)

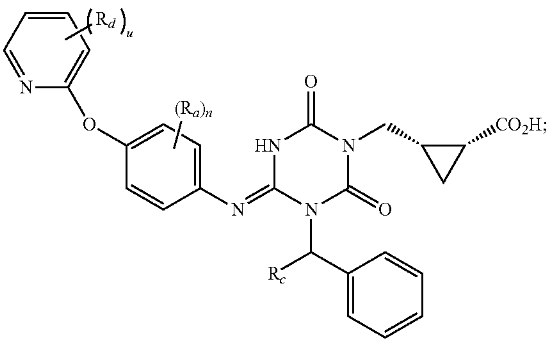

or the compound of formula (I) is of the structure shown in formula (II-4):

(II-4)

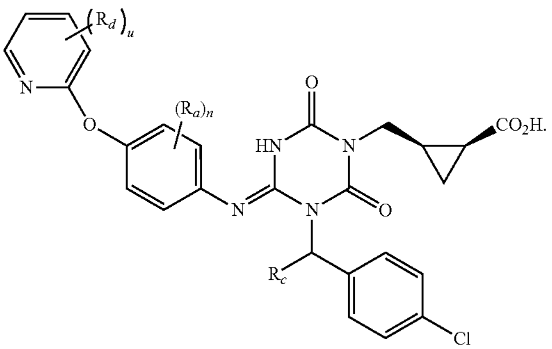

14. The compound according to claim 1, wherein the compound is selected from the group consisting of

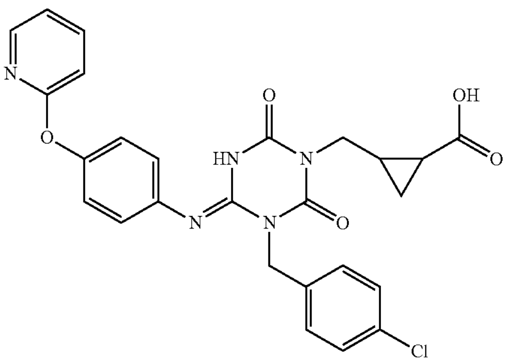

-continued

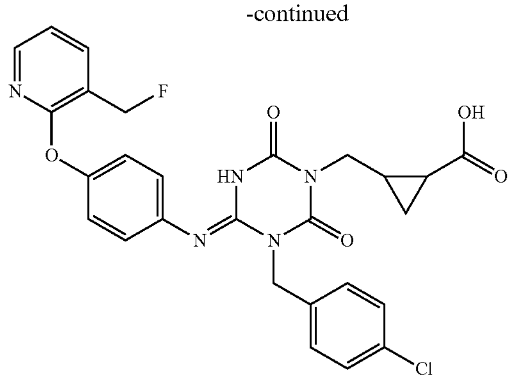

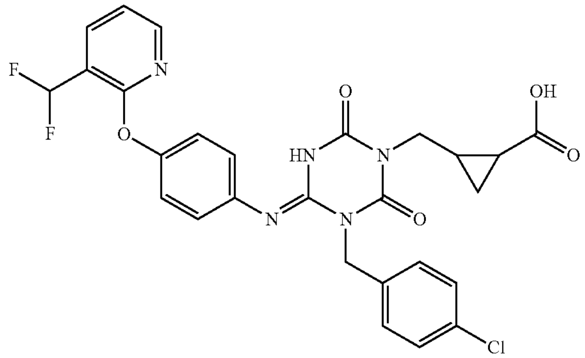

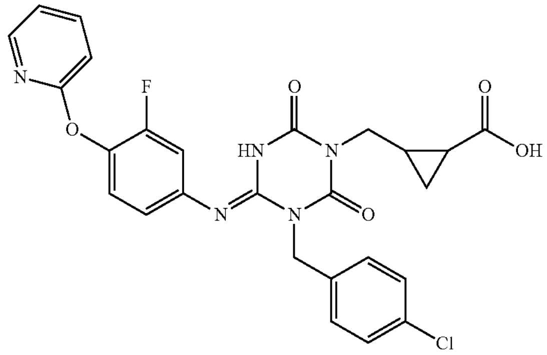

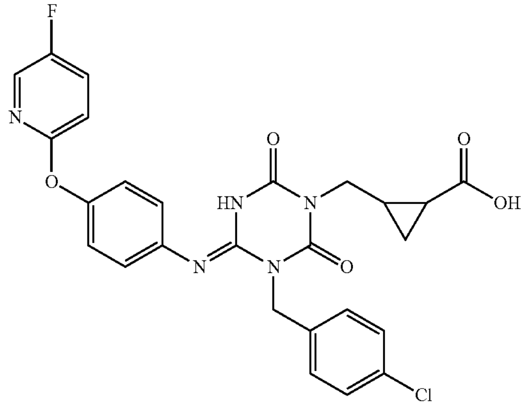

-continued

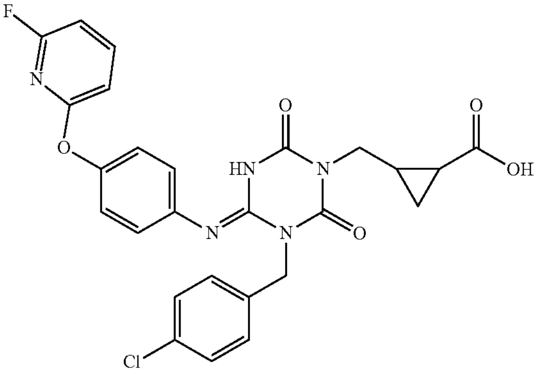

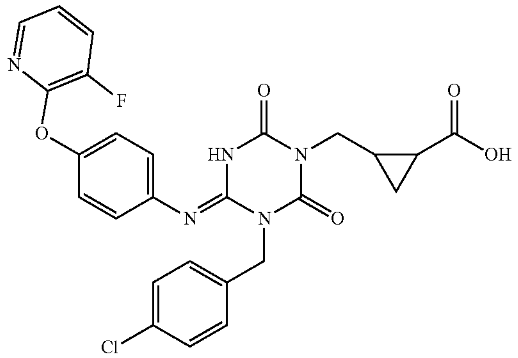

and

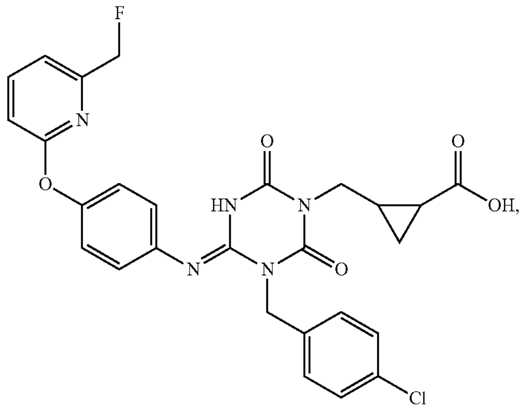

or the pharmaceutically acceptable salt thereof, or the stereoisomer thereof.

15. The compound according to claim 1, wherein the compound is selected from the group consisting of

| | |
|---|---|
| (±) cis-2-((3-(4-chlorobenzyl)-2,6-dioxo-4-(4-(pyridin-2-yloxy)phenylimino)-1,3,5-triazin-1-yl)methyl)cyclopropanecarboxylic acid | (±) trans-2-((3-(4-chlorobenzyl)-2,6-dioxo-4-(4-(pyridin-2-yloxy)phenylimino)-1,3,5-triazin-1-yl)methyl)cyclopropanecarboxylic acid |
| (±) cis-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((3-(fluoromethyl)pyridin-2-yl)oxy)phenyl)imino)-2,6-dioxo-1,3,5-triazin-1-yl)methyl)cyclopropan-1-carboxylic acid |

-continued

| | |
|---|---|
| (±) cis-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid | (±) trans-2-((3-(4-chlorobenzyl)-4-((3-((3-fluoro-4-(pyridin-2-oxy)phenyl)imino)-2,6-dioxo-1,3,5-triazin-1-yl)methyl)cyclopropan-1-carboxylic acid |
| (±) cis-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((5-fluoropyridin-2-yl)oxy)phenyl)imino)-2,6-dioxo-1,3,5-triazin-1-yl)methyl)cyclopropan-1-carboxylic acid |
| (±) cis-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((3-difluoromethyl)pyridin-2-yl)oxy)phenyl)imino)-2,6-dioxo-1,3,5-triazin-1-yl)methyl)cyclopropan-1-carboxylic acid |
| (±) cis-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((6-fluoropyridin-2-yl)oxy)phenyl)imino)-2,6-dioxo-1,3,5-triazin-1-yl)methyl)cyclopropan-1-carboxylic acid |
| (±) cis-2-((3-(4-chlorobenzyl)-4-((4-((3-fluoropyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((3-fluoropyridin-2-yl)oxy)phenyl)imino)-2,6-dioxo-1,3,5-triazin-1-yl)methyl)cyclopropan-1-carboxylic acid |
| (±) cis-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid | (±) trans-2-((3-(4-chlorobenzyl)-4-((4-((6-fluoromethyl)pyridin-2-yl)oxy)phenyl)imino)-2,6-dioxo-1,3,5-triazin-1-yl)methyl)cyclopropan-1-carboxylic acid, or the pharmaceutically acceptable salt thereof, or the stereoisomer thereof. |

16. The compound according to claim 1, wherein the compound is selected from the group consisting of

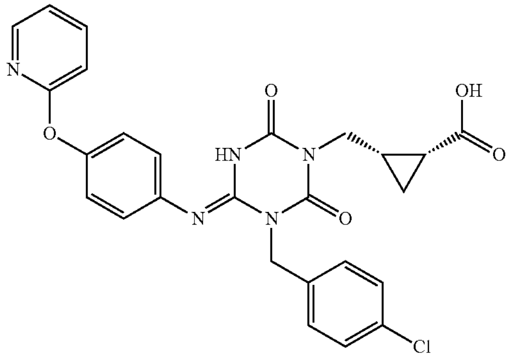

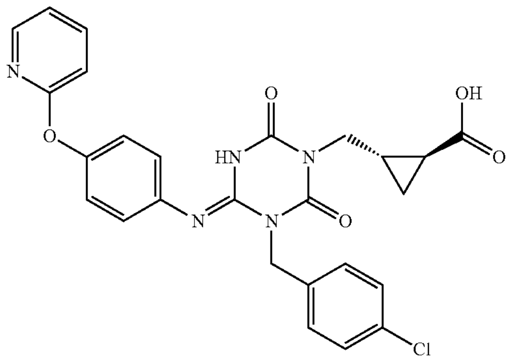

-continued

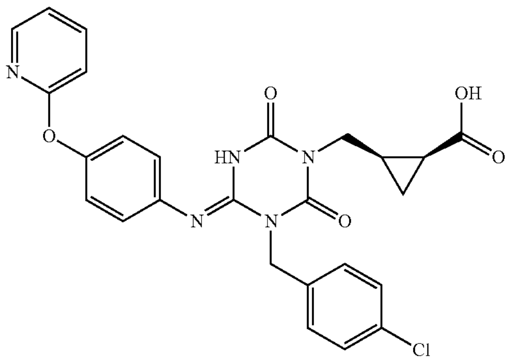

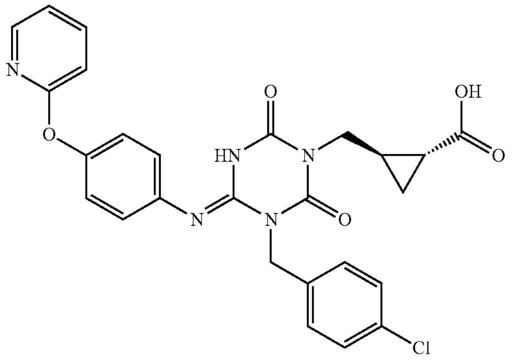

-continued
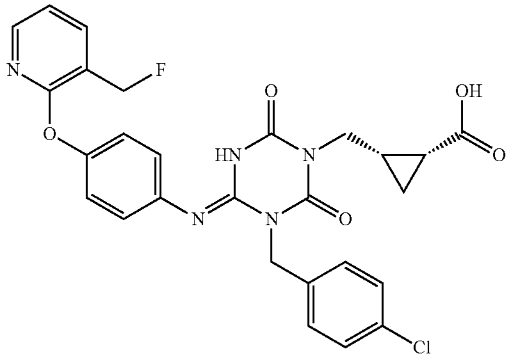
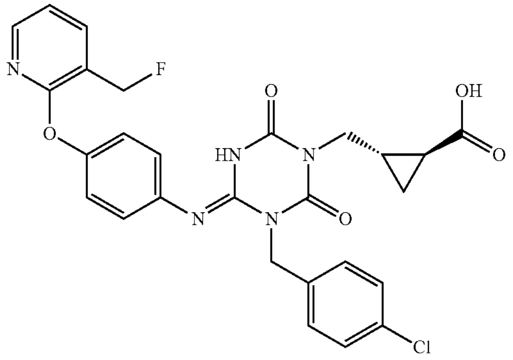
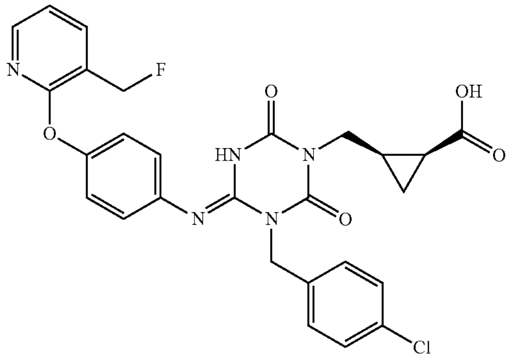
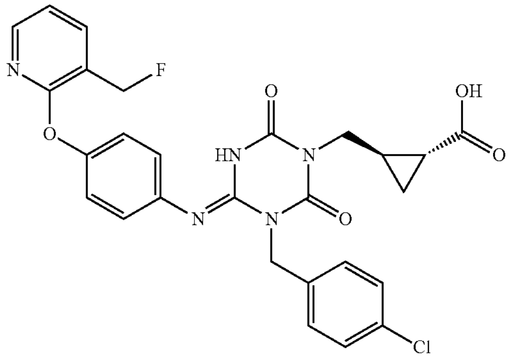
-continued
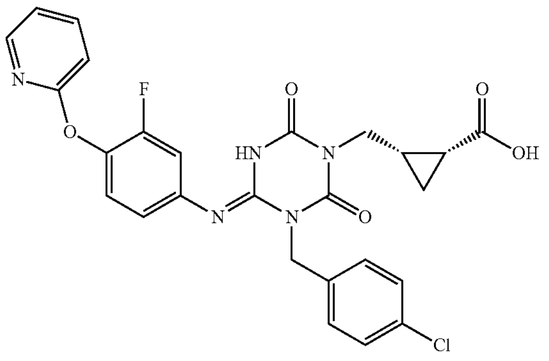
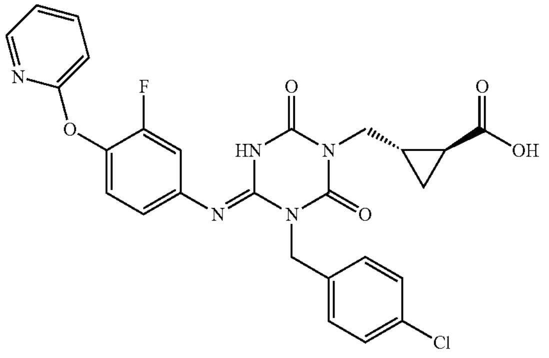
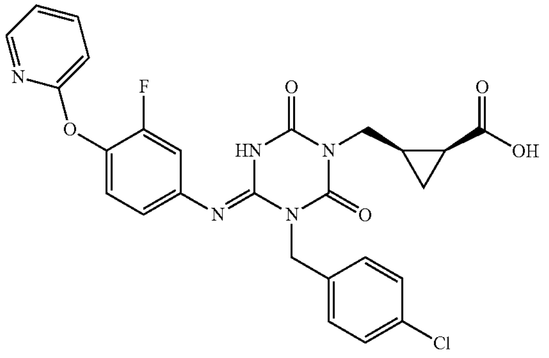
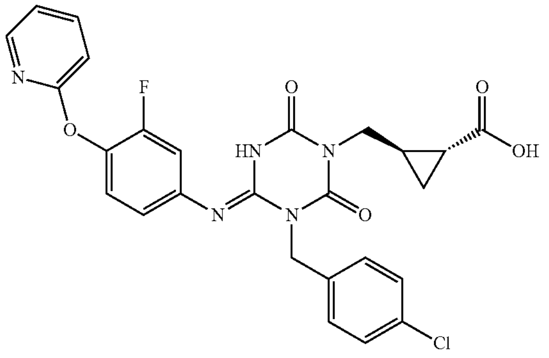

-continued
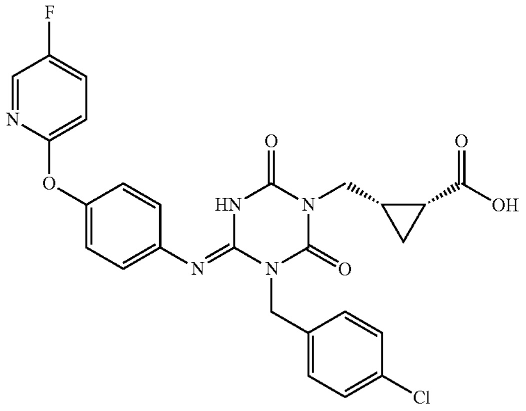
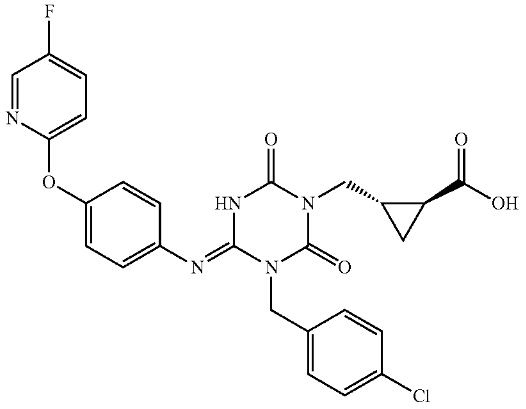
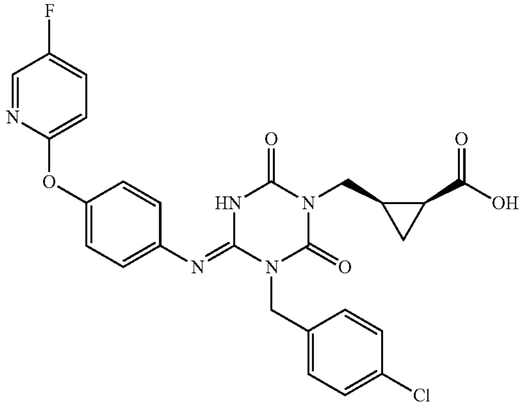
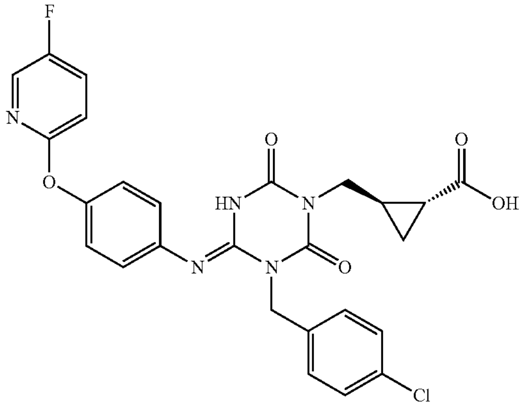
-continued
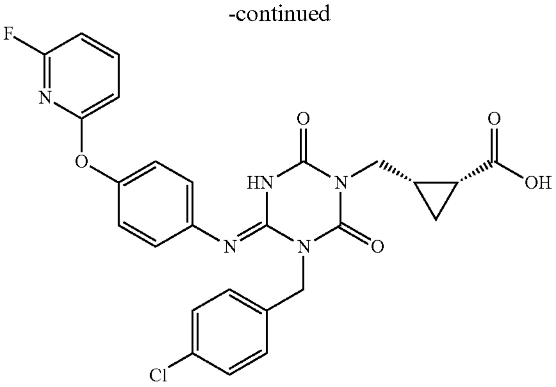
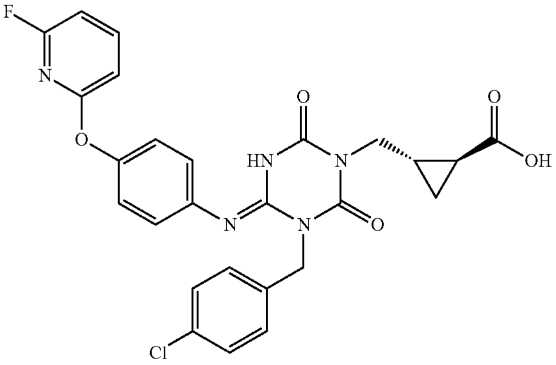
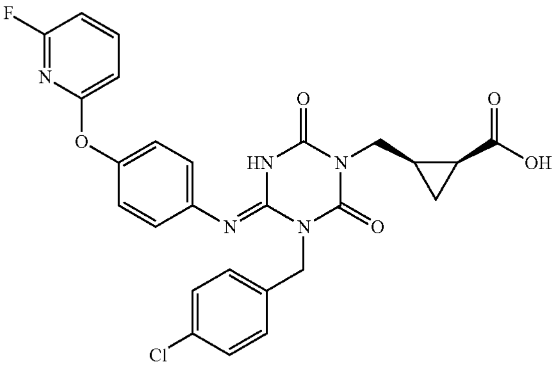
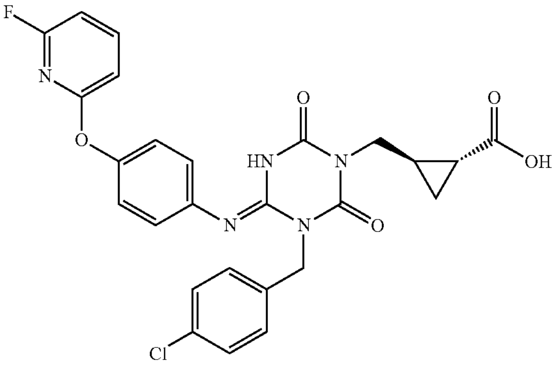

-continued
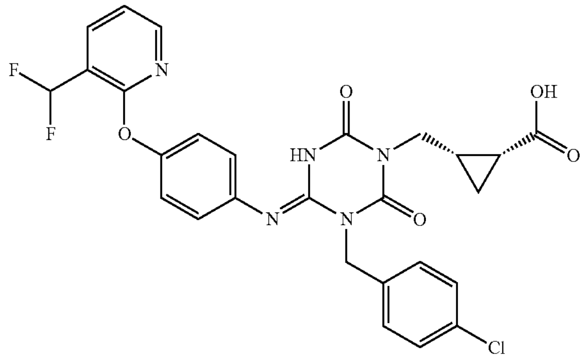
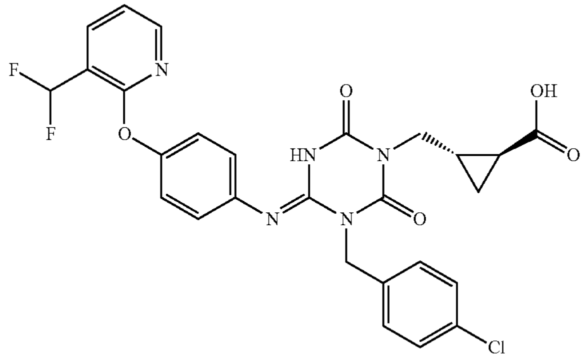
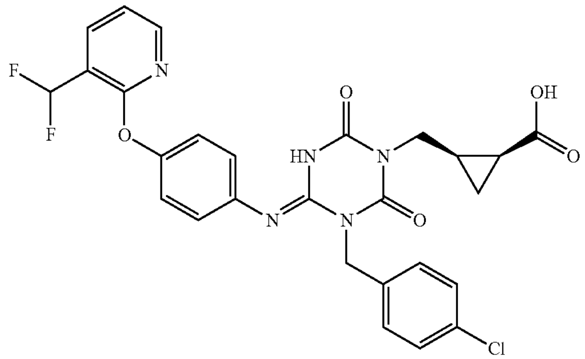
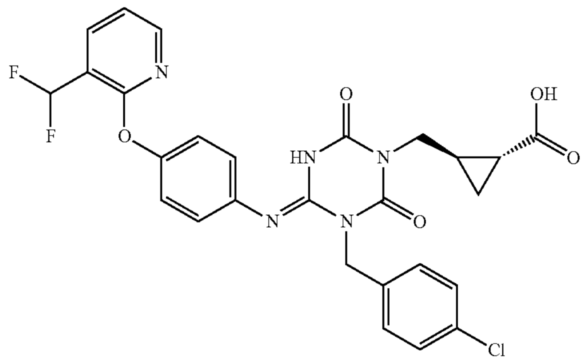
-continued
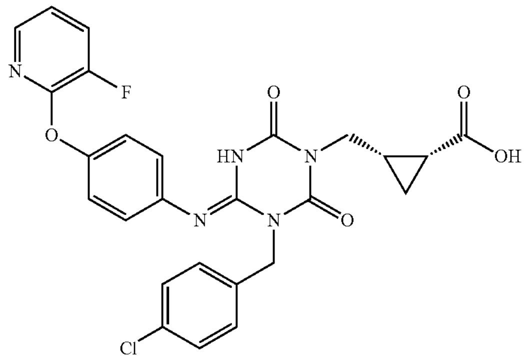
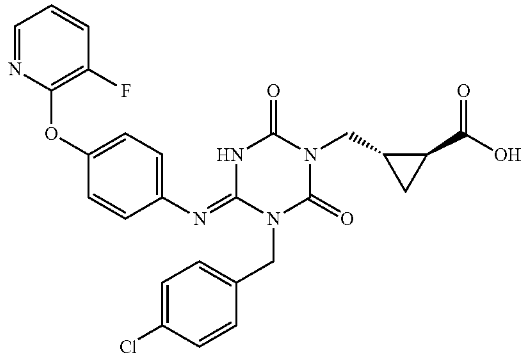
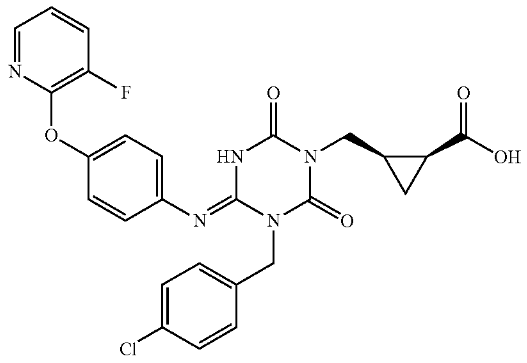
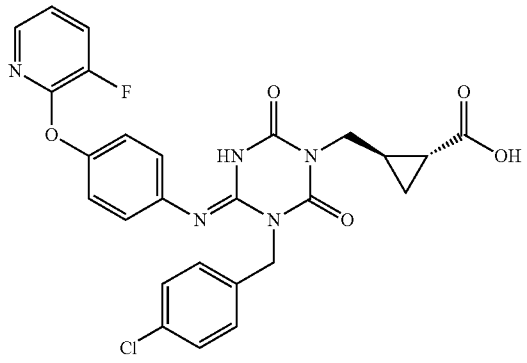

-continued

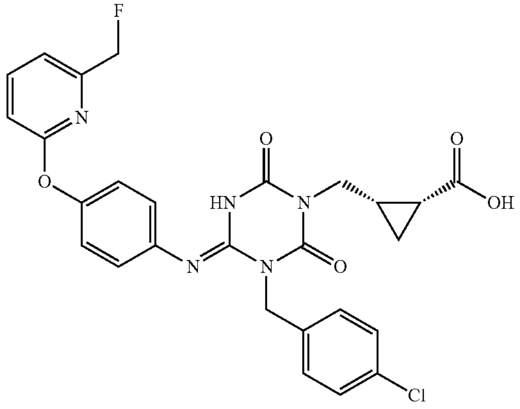

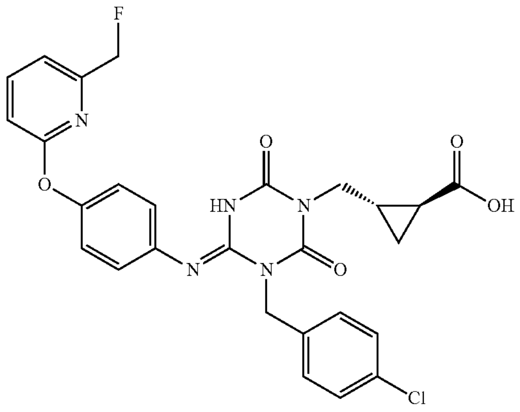

-continued

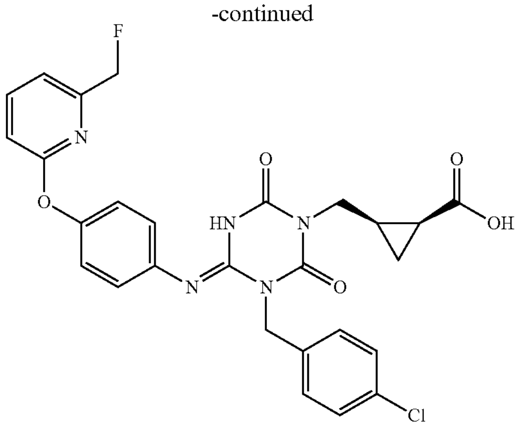

and

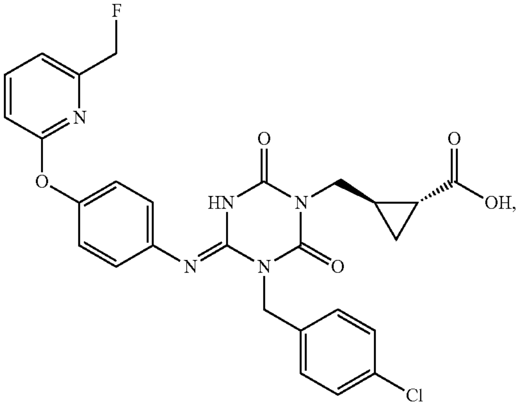

or the pharmaceutically acceptable salt thereof, or the stereoisomer thereof.

17. A pharmaceutical composition comprising:

1) The compound, or the pharmaceutically acceptable salt thereof, or the stereoisomer thereof according to claim 1; and 2) A pharmaceutically acceptable carrier.

18. A method of treating a disease associated with P2X3 activity or with P2X2/3 activity comprising administering a therapeutically effective amount of the compound, or the pharmaceutically acceptable salt thereof, or the stereoisomer thereof according to claim 1 to a subject in need thereof.

19. The method according to claim 18, wherein the disease associated with P2X3 activity or with P2X2/3 activity is pain, a urinary tract disorder, a gastrointestinal disorder, cancer, an immune-related disease, cough, depression, anxiety, or a stress-related disorder.

* * * * *